US008679809B2

(12) United States Patent
Chan et al.

(10) Patent No.: US 8,679,809 B2
(45) Date of Patent: Mar. 25, 2014

(54) CELL-MATRIX MICROSPHERES, METHODS FOR PREPARATION AND APPLICATIONS

(75) Inventors: Barbara Pui Chan, Ap Lei Chau (HK); Godfrey Chi-Fung Chan, Causeway Bay (HK); Hoi Ling Wong, Ma On Shan (HK); Pik To Cheung, Hung Hom (HK); Song-Eng Kathryn Cheah, 5G Tam Gardens (HK); Danny Chan, Ap Lei Chau (HK)

(73) Assignee: The University of Hong Kong, Hong Kong (HK)

( * ) Notice: Subject to any disclaimer, the term of this patent is extended or adjusted under 35 U.S.C. 154(b) by 1293 days.

(21) Appl. No.: 11/750,863

(22) Filed: May 18, 2007

(65) Prior Publication Data

US 2008/0031858 A1 Feb. 7, 2008

Related U.S. Application Data

(60) Provisional application No. 60/801,975, filed on May 19, 2006.

(51) Int. Cl.
*C12N 11/04* (2006.01)

(52) U.S. Cl.
USPC .......................................... 435/177; 424/93.7

(58) Field of Classification Search
None
See application file for complete search history.

(56) References Cited

U.S. PATENT DOCUMENTS

| | | | |
|---|---|---|---|
| 5,916,790 A * | 6/1999 | Enevold ......................... | 435/178 |
| 6,274,341 B1 | 8/2001 | Bailey et al. | |
| 6,451,060 B2 * | 9/2002 | Masuda et al. .............. | 623/23.72 |
| 6,905,875 B2 * | 6/2005 | Yu et al. ......................... | 435/395 |
| 2007/0292514 A1 * | 12/2007 | Chan Pui et al. .............. | 424/484 |

FOREIGN PATENT DOCUMENTS

| | | |
|---|---|---|
| WO | WO 97/15195 | 5/1997 |
| WO | WO 02/062357 | 8/2002 |

OTHER PUBLICATIONS

Kim et al, Int. J. Hematol, 2003; 78(2):126-132.*
Bancel and Hu, "Confocal laser scanning microscopy examination of cell distribution in macroporous microcarriers", *Biotechnol. Prog.*, 12(3):398-402 (1996).
Batorsky, et al., "Encapsulation of adult human mesenchymal stem cells within collagen-agarose microenvironments", *Biotechnol Bioeng.*, 92(4):492-500 (2005).
Bergeret-Galley, et al., "The value of a new filler material in corrective and cosmetic surgery: DermaLive and DermaDeep", *Aesthetic Plast. Surg.*, 25(4):249-55 (2001).
Bonaros, et al., "Cell therapy for ischemic heart disease", *Panminerva Med.*, 46(1):13-23 (2004).
Chia, et al., "Engineering microenvironment for expansion of sensitive anchorage-dependent mammalian cells", *J. Biotechnol.*, 118(4):434-47 (2005).
Coats, et al., "Requirement of p27Kip1 for restriction point control of the fibroblast cell cycle", *Science*, 272(5263):877-80 (1996).
Corcos, et al., "Multicenter randomized clinical trial comparing surgery and collagen injections for treatment of female stress urinary incontinence", *Urology*, 65(5):898-904 (2005).
Crevensten, et al., "Intervertebral disc cell therapy for regeneration: mesenchymal stem cell implantation in rat intervertebral discs", *Ann. Biomed. Eng.*, 32(3):430-4 (2004).
Durrschmid, et al., "Scalable inoculation strategies for microcarrier-based animal cell bioprocesses", *Biotechnol. Bioeng.*, 83(6):681-6 (2003).
Geserick, et al., "Enhanced productivity during controlled proliferation of BHK cells in continuously perfused bioreactors", *Biotechnol. Bioeng.*, 69(3):266-74 (2000).
Grohn, et al., "Collagen-coated Ba(2+)-alginate microcarriers for the culture of anchorage-dependent mammalian cells", *Biotechniques*, 22(5):970-5 (1997).
Jenkins and Hovey, "Temperature control of growth and productivity in mutant chinese-hamster ovary cells synthesizing a recombinant protein", *Biotechnol. Bioeng.*, 42(9):1029-36 (1993).
Kastan, et al., "Participation of p53 protein in the cellular response to DNA damage", *Cancer Res.*, 51(23 Pt 1):6304-11 (1991).
Ko and Prives, "p53: puzzle and paradigm", *Genes Dev.*, 10(9):1054-72 (1996).
Li, et al., "Chitosan/gelatin composite microcarrier for hepatocyte culture", *Biotechnol. Lett.*, 26(11):879-83 (2004).
Li, et al., "Differential damage and recovery of human mesenchymal stem cells after exposure to chemotherapeutic agents", *Br. J. Haematol.*, 127(3):326-34 (2004).
Liu, et al., "Bioreactor microcarrier cell culture system (Bio-MCCS) for large-scale production of autologous melanocytes", *Cell Transplant.*, 13(7-8):809-16 (2004).
Mazur, et al., "A novel autoregulated proliferation-controlled production process using recombinant CHO cells", *Biotechnol. Bioeng.*, 65(2):144-50 (1999).
Mercier, et al., "Poly(lactide-co-glycolide) microspheres as a moldable scaffold for cartilage tissue engineering", *Biomaterials*, 26(14):1945-52 (2005).
Mercille, et al., "Induction of apoptosis in oxygen-deprived cultures of hybridoma cells", *Cytotechnology*, 15(1-3):117-28 (1994).
Muschler, et al., "Engineering principles of clinical cell-based tissue engineering", *J. Bone Joint Surg. Am.*, 86-A(7):1541-58 (2004).
Nuttelman, et al., "Synthetic hydrogel niches that promote hMSC viability", *Matrix Biol.*, 24(3):208-18 (2005).

(Continued)

*Primary Examiner* — Allison Ford
(74) *Attorney, Agent, or Firm* — Pabst Patent Group LLP

(57) ABSTRACT

A method has been developed to produce stable cell-matrix microspheres with up to 100% encapsulation efficiency and high cell viability, using matrix or biomaterial systems with poor shape and mechanical stability for applications including cell therapeutics via microinjection or surgical implantation, 3D culture for in vitro expansion without repeated cell splitting using enzymatic digestion or mechanical dissociation and for enhanced production of therapeutic biomolecules, and in vitro modeling for morphogenesis studies. The modified droplet generation method is simple and scalable and enables the production of cell-matrix microspheres when the matrix or biomaterial system used has low concentration, with slow phase transition, with poor shape and mechanical stability.

19 Claims, 19 Drawing Sheets

(56) References Cited

OTHER PUBLICATIONS

Okamoto, et al., "Clonal heterogeneity in differentiation potential of immortalized human mesenchymal stem cells", *Biochem. Biophys. Res. Commun.*, 295(2):354-61 (2002).

Orive, et al., "History, challenges and perspectives of cell microencapsulation", *Trends Biotechnol.*, 22(2):87-92 (2004).

Overstreet, et al., "Collagen microcarrier spinner culture promotes osteoblast proliferation and synthesis of matrix proteins", *In Vitro Cell Dev. Biol. Anim.*, 39(5-6):228-34 (2003).

Pittenger and Martin, "Mesenchymal stem cells and their potential as cardiac therapeutics", *Circ. Res.*, 95(1):9-20 (2004).

Pittenger, et al., "Multilineage potential of adult human mesenchymal stem cells", *Science*, 284(5411)143-7 (1999).

Ponce, et al., "Microcapsules prepared with different biomaterials to immobilize GDNF secreting 3T3 fibroblasts", *Int. J. Pharm.*, 293(1-2):1-10 (2005).

Romanov, et al., "Mesenchymal stem cells from human bone marrow and adipose tissue: isolation, characterization, and differentiation potentialities", *Bull. Exp. Biol. Med.*, 140(1):138-43 (2005).

Sanchez-Bustamante, et al., "Heterologous protein production capacity of mammalian cells cultivated as monolayers and microtissues", *Biotechnol. Bioeng.*, 93(1):169-80 (2006).

Sun, et al., "Attachment kinetics of Vero cells onto CT-3 microcarriers", *J. Biosci. Bioeng.*, 90(1):32-6 (2000).

Suzuki and Ollis, "Enhanced antibody production at slowed growth rates: experimental demonstration and a simple structured model", *Biotechnol. Prog.*, 6(3):231-6 (1990).

Tatard, et al., "Pharmacologically active microcarriers: a tool for cell therapy", *Biomaterials*, 26(17):3727-37 (2005).

Tatard, et al., "Combining polymeric devices and stem cells for the treatment of neurological disorders: a promising therapeutic approach", *Curr. Drug Targets*, 6(1):81-96 (2005).

Uludag, et al., "Technology of mammalian cell encapsulation", *Adv. Drug Deliv. Rev.*, 42(1-2):29-64 (2000).

Voigt, et al., "Human recombinant EGF protein delivered by a biodegradable cell transplantation system", *Tissue Eng.*, 8(2):263-72 (2002).

Watanabe, et al., "Regulation of cell cycle and productivity in NS0 cells by the over-expression of p21CIP1", *Biotechnol. Bioeng.*, 77(1):1-7 (2002).

Wurm, "Production of recombinant protein therapeutics in cultivated mammalian cells", *Nat. Biotechnol.*, 22(11):1393-8 (2004).

Zhang, et al., "Proliferation, viability, and metabolism of human tumor and normal cells cultured in microcapsule", *Appl. Biochem. Biotechnol.*, 134(1):61-76 (2006).

Zimmermann, et al., "Fabrication of homogeneously cross-linked, functional alginate microcapsules validated by NMR-, CLSM- and AFM-imaging", *Biomaterials*, 24(12):2083-96 (2003).

\* cited by examiner

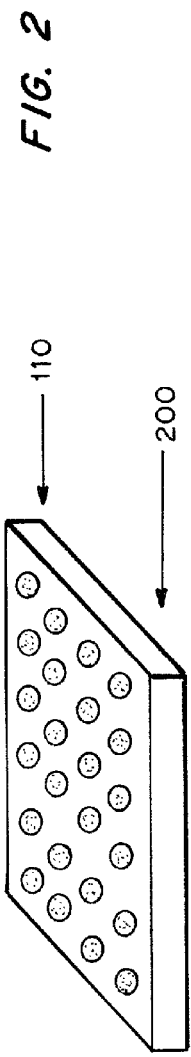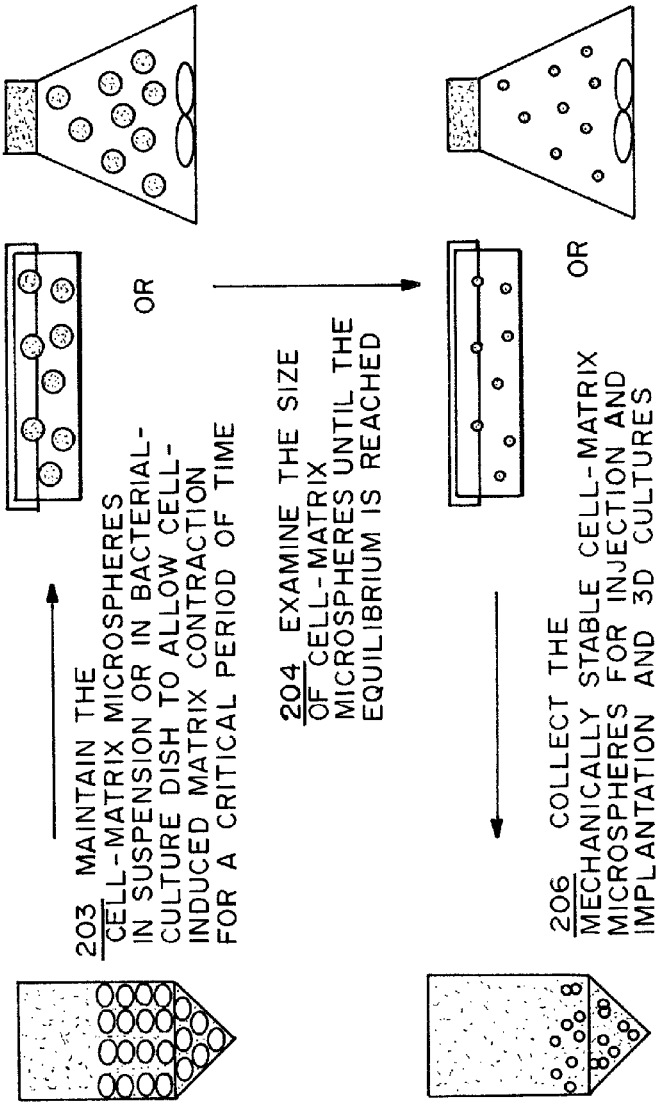
FIG. 2

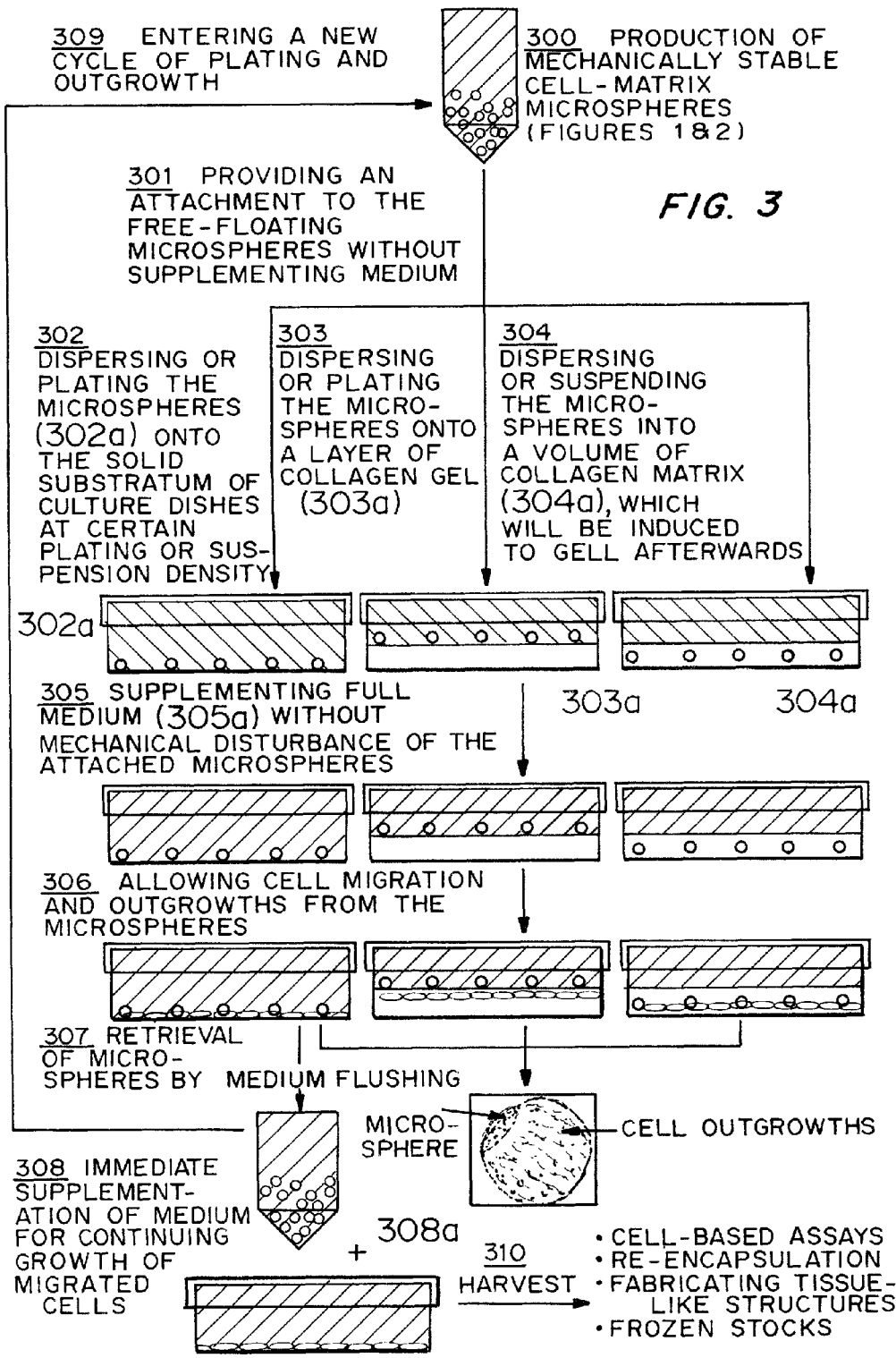

CELL-MATRIX MICROSPHERES, METHODS FOR PREPARATION AND APPLICATIONS

CROSS-REFERENCE TO RELATED APPLICATIONS

This application claims priority to U.S. Ser. No. 60/801,975 filed May 19, 2006.

FIELD OF INVENTION

The present invention relates generally to cell-matrix microspheres, associated products, methods for preparation and applications. More specifically, it related to methods producing cell-matrix microspheres and immobilizing living cells, methods and processes for culturing these cells; methods and processes for using these microspheres as therapeutics, as three dimensional ("3D") microcarriers, and for production of biomolecules such as therapeutic proteins, in a more efficient and economical manner.

BACKGROUND OF INVENTION

Cell-based therapy provides a minimally invasive approach by local injection at the site of defect via microsyringe needles and presents a promising approach for tissue repair and regenerative medicine. However, technological challenges associated with the localization, long term viability, host tissue-integration and functional remodeling (Tatard, et al., Curr. Drug Targets, 6(1):81-96 (2005); Tatard, et al., Biomaterials, 26(17):3727-37 (2005); Pittenger and Martin, Circ. Res., 95(1):9-20 (2004); Bonaros, et al., Panminerva Med., 46(1):13-23 (2004)) of the injected cells, and injectability and mechanical stability of the carriers (Crevensten, et al., Ann. Biomed. Eng. 32(3):430-4 (2004)) need to be resolved before clinical applications can be successfully achieved.

Microencapsulation entraps cells within the confinement of a semi-permeable membrane or a homologous solid. It has been used for many years to aid immunoisolation during allogenic or xenogenic cell transplantation (Uludag et al., Adv. Drug Deliv. Rev., 42(1-2):29-64 (2000); Orive, et al., Trends Biotechnol., 22(2):87-92 (2004)). Sodium alginate dominates the field while other materials such as agarose (Batorsky, et al., Biotechnol. Bioeng., 92(4):492-500 (2005)) and polyethylene glycol (PEG) (Nuttelman, et al., Matrix Biol., 24(3):208-18 (2005)) are also used. None of these materials, if unmodified, support cell attachment and growth (Grohn, et al., Biotechniques, 22(5):970-5 (1997); Zimmerman, et al., Biomaterials, 24(12):2083-96(2003); Nuttelman, et al., Matrix Biol. 24(3):208-18 (2005)) thus requiring supplementation of natural extracellular matrix such as collagen for improvement (Grohn, et al., Biotechniques, 22(5): 970-5 (1997); Batorsky, et al., Biotechnol. Bioeng. 92(4):492-500 (2005)). Furthermore, since these systems avoid direct contact of the delivered cells with the host tissue, they do not allow cell migration and penetration. This prevents their use in regenerative medicine and tissue engineering, which entails host-implant integration at cellular level. Natural extracellular matrices such as collagen, fibrin and hyaluronic acid are suitable materials supporting cell growth (Yannas, Natural Materials, Ratner, et al. editors, Biomaterials Sciences—An introduction to materials in medicine, California, Academic Press, pp. 84-93 (1996)). However, there is no microencapsulation system for these materials because of their poor mechanical and shape stability (Yannas, Natural Materials, Ratner, et al. editors, Biomaterials Sciences—An introduction to materials in medicine, California, Academic Press, pp. 84-93 (1996); Crevensten, et al., Ann. Biomed. Eng., 32(3):430-4 (2004); Zhang, et al., Appl. Biochem. Biotechnol., 134(1):61-76 (2006), which is incompatible with the existing microencapsulation techniques (Uludag, et al., Adv. Drug Deliv. Rev., 42(1-2):29-64 (2000)).

Existing encapsulation techniques include formation of emulsions with an oil phase and generation of cell-containing droplets in a stirred collection bath using a custom-made droplet generator, or injection of cells into preformed matrix microspheres or microcapsules using a microinjector (Grohn, et al., Biotechniques, 22(5):970-5 (1997); Batorsky, et al., Biotechnol. Bioeng., 92(4):492-500 (2005)). However, these methods encounter problems when the matrix materials are low in concentration, or with poor shape and mechanical stability such as collagen gel or hyaluronic acid gel. First, the cell-matrix droplets or emulsions formed barely survive the shear stress generated upon stirring during emulsification or stirring in the liquid collection bath. Second, stirring is required immediately after addition of the cell-matrix phase to mix well with the oil phase during emulsification and to prevent the cell-matrix droplets from fusing together during droplet generation. The does not allow sufficient time for the formation of cell-matrix microspheres if the phase transition of the matrix takes a longer time and fragmentizes the microspheres, leading to low encapsulation efficiency.

Using living organisms with biosynthetic capability for large and industrial scale production of useful biomolecules such as therapeutic protein is commonly used in biotechnology. Although E. coli and yeasts have been used for this purpose, the resulting molecules may differ from the natural products because of the absence of co- and post-modifications mechanisms in these microorganisms. Mammalian cells are therefore particularly good sources for proteins and vaccines. Culturing cells in suspensions can attain high efficiency, reduce cost and favor mass production of therapeutic proteins. However, not all cells grow successfully in suspension, only cells such as hybridomas and tumor cells. Microcarrier technology has been developed for decades to enable large scale 3D culture by providing significantly increased surface area that is particularly advantageous for anchorage dependent eukaryotes. Microcarriers have been used for large scale cell culture as early as the 70's. The first generation microcarrier, CYTODEX®, dextran microspheres with cationic surface, has been used to scale up cell cultures by dramatically increasing the total surface area for cell binding. The technology evolved in the 80's to include collagen-coated dextran beads, for better attachment and growth of cells and higher yield). There has been a trend in coating or mixing the solid microcarriers with natural extracellular matrix of cells such as collagen-coated alginate beads (Grohn, et al., Biotechniques, 22(5):970-5 (1997)), gelatin-coated poly-lactic-glycolic acid (PLGA) beads (Voigt, et al., Tissue Eng., 8(2):263-72 (2002)) and gelatin-chitin composite beads (Li, et al., Biotechnol. Lett., 26(11):879-83 (2004)), or crosslinking with natural peptide sequence governing cell adhesion and attachment such as RGD modified poly(ethylene glycol) (Nuttelman, et al., Matrix Biol., 24(3):208-18 (2005)) to improve cell attachment and growth. This has led to development of newer generations of microcarriers, CULTISPHER® G, which are either solid (Liu, et al., Cell Transplant., 13(7-8):809-16 (2004)) or porous (Bancel and Hu, Biotechnol. Prog., 12(3):398-402 (1996)) gelatin beads, and CELLAGEN®, which are porous collagen beads (Overstreet, et al., In Vitro Cell Dev. Biol. Anim., 39(5-6):228-34 (2003)). However, these systems employ technologically demanding fabrication process for the bead preparations, making the commercial preparations costly. The bead preparation has to be separated from the cell attachment procedure since most of the bead fabrication system employ harsh conditions such as high temperature, freeze-drying, organic solvent extraction and chemical crosslinking treatment that cells do not survive. Moreover, the cell attachment procedure is a rate-limiting step of the microcarrier culture system (Sun, et al., *J. Biosci. Bioeng.*, 90(1):32-6 (2000)) requiring prolonged culture for cell attachment to the solid surfaces or cell penetration into the porous beads (Bancel and Hu, *Biotechnol. Prog.*, 12(3): 398-402 (1996)). As a result, simple bead preparation using natural extracellular matrix materials without harsh fabrication conditions and prolonged cell attachment procedures will improve the efficiency and reduce the cost of the microcarrier culture system.

It is generally accepted that 3D culture provides a platform for cells to proliferate rapidly in an unrestricted manner (Geserick, et al., *Biotechnol. Bioeng.*, 69(3):266-74 (2000)) for scaling up (Durrschmid, et al., *Biotechnol. Bioeng.*, 83(6): 681-6 (2003)). However, the productivity of actively and unrestrictedly proliferating cells is usually low because these cells may not synthesize proteins at a maximal rate outside their tissue-specific microenvironment and in actively proliferating cells, most of the metabolic energy is activated to reproduction rather than synthetic activities (Sanches-Bustamante, et al., *Biotechnol. Bioeng.*, 93(1):169-180 (2005)). Controlled proliferation technologies such as starvation of cells for essential nutrient or addition of DNA synthesis inhibitors (Suzuki and Ollis, *Biotechnol. Prog.*, 6(3):231-6 (1990)), isolation of specific cell lines such as temperature sensitive CHO cells, which produce more proteins upon temperature shift to 39° C. (Jenkins and Hovey, *Biotechnol. Bioeng.*, 42(9):1029-36 (1993)) and genetic manipulation with growth cycle controlling genes such as over-expressing tumor suppressor genes p53 (Kastan, et al., *Cancer Research*, 51:6304-11 (1991)), p 21 (Watanabe, *Biotechnol. Bioeng.*, 77:1-7 (2002)) and p 27 (Coats, et al., *Science*, 272:877-80 (1996)), are usually employed to enhance the protein productivity of cells (U.S. Pat. No. 6,274,341 to Bailey, et al.; Wurm, *Nature Biotechnol.*, 2(11):1393-1398 (2004)). However, these proliferation controlling strategies lead to reduced cell viability (Mercille, et al., *Cytotechnology*, 15(1-3):117-28 (1994)) and increased apoptosis (Ko and Prives, *Genes Dev.*, 10(9):1054-72 (1996)). Co-expressing the cell cycle controlling tumor suppressor genes with anti-apoptotic genes such as bcl-2 has been used to improve the cell viability problem (U.S. Pat. No. 6,274,341 to Bailey, et al.). However, this system requires complicated designs for the vector systems and complicated genetic manipulation that interfaces the cell metabolism internally. Moreover, auto-regulated control for biphasic proliferation and production cycles has been achieved by using external repressable agent, tetracycline switch system (Mazur, et al., *Biotechnol. Bioeng.*, 65:144-150 (1999)) to preserve the inducible growth-arresting production phase when the optimal cell density is reached so that a longer window for enhanced productivity for 7 days can be achieved. The advantages of this system include the use of external agents that do not interfere with the overall metabolism of cells but the problems are the downstream purification procedures eliminating this antibiotic, the genetic instability introduced by genetic manipulation as well as the instability of tetracycline in cultures. Recently, 3D multi-cellular microtissue cultures using a hanging-drop method with enhanced protein productivity in mammalian cells have been developed (Sanchez-Bustamante, et al., *Biotechnol. Bioeng.*, 93(1):169-180 (2005)).

It is therefore an object of the invention to provide methods for making cell microcarriers that are relatively inexpensive, efficient and favorable to cell viability, controlled proliferation and production of biomolecules, and the resulting cell matrix microcarriers.

It is a further object of the invention to provide methods for use thereof in cell therapy and tissue engineering and manufacturing of biomolecules.

SUMMARY OF THE INVENTION

A method has been developed to produce stable cell-matrix microspheres with up to 100% encapsulation efficiency and high cell viability, using matrix or biomaterial systems with poor shape and mechanical stability for applications including cell therapeutics via microinjection or surgical implantation, 3D culture for in vitro expansion without repeated cell splitting using enzymatic digestion or mechanical dissociation and for enhanced production of therapeutic biomolecules, and in vitro modelling for morphogenesis studies. The modified droplet generation method is simple and scalable and enables the production of cell-matrix microspheres when the matrix or biomaterial system used has low concentration, with slow phase transition, with poor shape and mechanical stability.

The method uses a formulation including cells, a first extracellular matrix (ECM), and other biomolecules. In the preferred embodiment, the first ECM, being capable of providing support to the cells, interacting with the cells to allow cell growth without introducing toxicity, and permitting cell migration and penetration, is a collagen, or other material that supports cell growth and migration and has phase transition properties at conditions mild enough to support cell survival, such as fibrin and hyaluronic acid. The composition can include a second ECM, such as a proteoglycan or GAG. These can interact in such a way that the interaction leads to a change in cellular responses in growth and differentiation and physical properties of microspheres such as the volume of the structures, ECM density, cell density, mechanical property and stability, etc. The composition can also include a growth-stimulating signal such as human serum, platelet rich plasma or other blood products. Therapeutic components such as anti-inflammatory drugs and antibiotics can also be incorporated in the composition.

The method of forming microspheres include the steps of mixing and dispensing the composition into liquid droplets in the right order and the right time with a dispensing unit. The pH of the first matrix is adjusted to be suitable for cell survival. The cell suspension and other biomolecules are mixed thoroughly with the matrix components as soon as possible to evenly distribute cells throughout the solution form of the matrix before accelerating phase transition. The liquid droplets are collected with a dry collection platform without mechanical disturbance. The platform has a surface property for maintaining the spherical shape of the liquid droplets, such as high surface tension. By maintaining the temperature low, the rate of matrix phase transition can be controlled as low as possible at a range between 2 minutes to 10 hours depending on the matrix concentration, preferably 30 minutes. The volume of the microspheres dispensed is preferably about 2.5 µl. The diameter of the dispensed liquid droplets is preferably 2 mm. In addition, the method comprises accelerating the rate of matrix phase transition after dispensing by raising the temperature at the collection platform preferably to 37° C. The matrix components of the liquid droplets are allowed to undergo phase transition to form cell-matrix microspheres for a period of time, sufficient for phase transition to reach equilibrium.

The microspheres are stabilized by collecting the cell-matrix microspheres from the collection platform with minimal mechanical disturbance; maintaining the microspheres free-floating in a first medium for an extended period of time until the size of the microspheres becomes substantially constant; and releasing the microspheres from the first medium. The microspheres can be maintained free-floating either by keeping in suspension status in non-adhesive culture dish such as a Petri dish, or by culturing the microspheres in spinner flask or rotating vessel bioreactors. The size and mechanical strength of the microspheres can be controlled by controlled by at least one of the following parameters: cell density, collagen concentration, serum concentration, composition of the ECM, ratio of the first and second ECM, volume of the liquid droplets, duration of the free-floating status of microspheres. Increasing cell density, decreasing matrix concentration or decreasing volume of liquid droplets decreases size and increases stability of cell-matrix microspheres.

A system for producing microspheres includes the composition described above, a dispensing unit for dispensing the composition into liquid droplets; and a collection platform for collecting the dispensed liquid droplets, comprising a surface with a surface property such that the spherical shape of the microspheres can be maintained; and for gelation of the matrix to form cell-matrix microspheres. The system can further comprise a control unit for controlling the dispensing speed and volume, as well as a temperature control unit for maintaining the temperature of the composition during dispensing and during phase transition of the matrix.

The cell-matrix microspheres consisting of undifferentiated and viable cells can be injected or implanted, for example, for tissue repair or regeneration. The method includes the steps of sedimenting the microspheres in a liquid for injection or implantation; adding the microsphere suspension in the container for injection or implantation; and injecting or implanting the microspheres into defective tissues in animals or humans such as a skin wound or an injured cartilage. In one embodiment, the method includes injecting or implanting the cell-matrix microspheres consisting of specifically differentiated and viable cells, wherein the matrix embeds these cells into defective tissues of animals or humans.

The cell matrix microspheres are also useful for 3D cultures. These have numerous advantages over the existing microcarrier systems. The system can be used to culture protein-secreting cells in physiologically relevant microenvironment with significantly increased protein productivity via matrix-induced proliferation control as compared to monolayer cultures with unrestricted proliferation.

BRIEF DESCRIPTION OF THE DRAWINGS

FIG. 2 is a flow chart showing the production of mechanically stable cell-matrix microspheres with controllable size.

FIG. 3 is a flow chart showing the method controlling of the cell migration from the cell-matrix microspheres.

DETAILED DESCRIPTION OF THE INVENTION

I. Definitions

Figure 1:
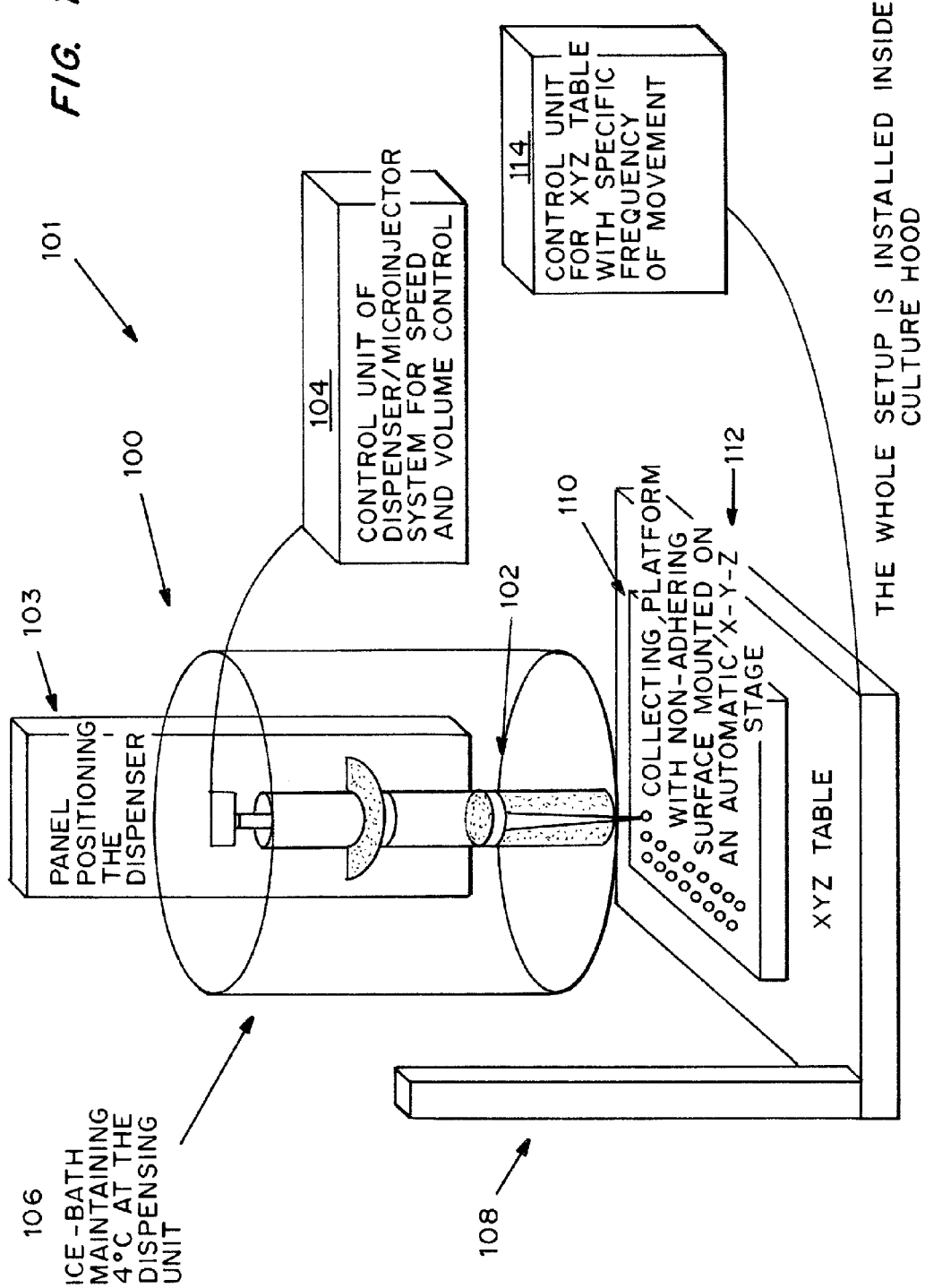
FIG. 1 is a schematic drawing showing the production setup for making cell-matrix microspheres.

As used herein, encapsulated in microspheres refers to formation of a nanofibrous microsphere having embedded therein cells as a result of a phase change of the material forming the microsphere.

As used herein, "ECM" refers to an extracellular matrix material, in pure, isolated, partially isolated, recombinant or synthetic form, or a synthetic material having comparable physical and biological properties to ECM As used herein a mechanically stable microsphere, is one that, after reaching equilibrium, can be mechanically manipulated by forceps and are resistant to the shear stress and turbulence generated during pipetting up and down at rapid rate such as 20 ml/min or even vortexed with maximal speed.

II. Materials for Manufacturing Cell-Matrix Microspheres

A method has been developed to produce stable cell-matrix microspheres with up to 100% encapsulation efficiency and high cell viability, using matrix or biomaterial systems with poor shape and mechanical stability for applications including cell therapeutics via microinjection or surgical implantation, 3D culture for in vitro expansion without repeated cell splitting using enzymatic digestion or mechanical dissociation and for enhanced production of therapeutic biomolecules, and in vitro modeling for morphogenesis studies. The modified droplet generation method is simple and scalable and enables the production of cell-matrix microspheres when the matrix or biomaterial system used has low concentration, with slow phase transition, with poor shape and mechanical stability. The method uses a formulation including cells, a first extracellular matrix (ECM), optionally a second ECM, and other biomolecules.

A. ECM Materials

The composition includes at least one ECM. The ECM must be capable of providing support to the cells, interacting with the cells to allow cell growth without introducing toxicity, and permitting cell migration and penetration, can be collagen of different types, such as type I, II, and III, or any materials that are good in supporting cell growth and migration and have phase transition properties at conditions mild enough to support cell survival, such as fibrin and hyaluronic acid. The collagen used can be of bovine origin such as those used in FDA-approved skin equivalents Integra® and Apligraf® and the soft tissue fillers or products that have been used clinically for wrinkle reduction such as DermaLive and DermaDeep (Bergeret-Galley, et al., *Aesthetic Plast. Surg.*, 25(4):249-55 (2001), or for urinary incontinence treatment (Corcos, et al., *Urology*, 65(5):898-904 (2005)). The ECM can be derived from either natural or synthetic sources, and it can be induced to reconstitute into solid form under specific conditions that are mild enough to support cellular survival and growth. The ECM can be produced from isolation or extraction from various animal sources, such as rat tail, porcine skin, bovine Achilles tendon, or human placenta. Preferably, the first ECM is isolated from different fractions during the extraction process, such as acid-soluble, pepsin-soluble, or insoluble fractions.

The composition can further comprise a second ECM, which can be a proteoglycan or glycosaminoglycan ("GAG") produced from shark cartilage, fibrin, elastin or hyaluronic acid. The first ECM can interact with living cells or with the second ECM in such a way that the interaction leads to a change in cellular responses in growth and differentiation and physical properties of microspheres such as the volume of the structures, ECM density, cell density, mechanical property and stability, etc.

The matrix components also include other hydrogels whose fabrication conditions are mild enough to maintain high cell viability after encapsulation without the use of organic solvents or other substances toxic to cells, and without harsh conditions, such as alginate gel which is gelled by addition of calcium.

B. Cells

The cells may be mature cells or stem cells from human or clinically feasible sources, such as autologous, allogeneic, fetal, embryonic and xenogenic sources. The cells can be of diverse origin. In preferred embodiments, cells are human bone marrow derived mesenchymal stem cells (hMSCs), human embryonic and fetal stem cells capable of therapeutic use, adult stem cells isolated from sources including but are not limited to human skin, GI tract, adipose tissue, placenta, and adult cells capable of therapeutic use such as those from healthy biopsies of the intervertebral discs, cartilage, muscles, skin, tendon and ligament, etc. The cells can be genetically manipulated to over-express one or more specific biomolecules such as proteins or physiologically active in secreting one or more specific biomolecules such as proteins, examples are HEK293 cells, 3T3 fibroblasts, osteosarcoma cells, C2C12 cell line, human bone marrow derived mesenchymal stem cells (hMSCs), etc. The cells can also be obtained from allogenic sources capable for therapeutic use, such as rabbit MSCs, mouse MSCs and other animal cells for therapeutic use in animal disease models. Preferably, the cells are bone marrow-derived mesenchymal stem cells (MSCs), either autologous or allogeneic from HLA-matched donors. Preferably, the mature cells are keratinocytes isolated from biopsies of healthy skin from burn patients; chondrocytes isolated from biopsies of healthy articular cartilage from osteoaarthritis patients; intervertebral disc cells isolated from biopsies of healthy discs from patients with severely degenerated discs; or Schwann cells isolated from autologous peripheral nerve grafts in patients with spinal cord or other CNS injuries.

The examples utilized HEK293 secreting GDNF as an example of production of biomolecules. Other cells such as 3T3 fibroblasts and CHO cells can be used while other useful biomolecules such as glycoproteins and proteoglycans can also be used.

C. Optional Growth Factors

The composition can also include a growth-stimulating signal such as human serum, platelet rich plasma or other blood products. Preferably, an additional factor affecting the differentiation of MSCs is included in the composition. Exemplary factors include TGF-beta for chondrogenic lineage.

D. Cell Culture Media

The aqueous media can be culture medium, with or without serum, buffered saline, or other liquid phase compatible with cell viability and with suitable ionic strength. Typical mediums include DMEM, DMEM-LG, MEM, and RPMI.

E. Optional Therapeutic, Prophylactic or Bioactive Agents

The formulation can also include therapeutic, prophylactic or diagnostic agents. For example, therapeutic components such as anti-inflammatory drugs and antibiotics can also be incorporated into the composition. Diagnostic agents such as dyes or radio-opaque agents can be incorporated. Preservatives can be included for storage.

III. Method of Making Cell-Matrix Microspheres

The system for producing microspheres includes the composition described above, a unit for dispensing the composition as liquid droplets; and a collection platform for collecting the dispensed liquid droplets, comprising a surface with a surface property such that the spherical shape of the microspheres can be maintained; and for gelation of the matrix to form cell-matrix microspheres. The substratum onto which the droplets are dispensed can be a parafilm wrapped or a gelatin coated, or other material having similar surface properties, plastic or metal or glass platform having a high surface tension to maintain the spherical shape of the droplets as much as possible. The system can further comprise a control unit for controlling the dispensing speed and volume, as well as a temperature control unit for maintaining the temperature of the composition during dispensing and during phase transition of the matrix.

The method of forming microspheres includes the steps of mixing and dispensing the composition into liquid droplets in the right order and the right time with a dispensing unit. The pH of the ECM matrix is adjusted to be suitable for cell survival. The first and the second matrix are mixed well if specific interaction between these components is needed. The cell suspension and other biomolecules are mixed thoroughly with the matrix components as soon as possible to evenly distribute cells throughout the solution forming the matrix before accelerating phase transition. The dispensing unit can be manual or automatic. The liquid droplets are collected with a dry collection platform without mechanical disturbance.

The platform has a surface property for maintaining the spherical shape of the liquid droplets, such as high surface tension. The dispensing environment is maintained at a temperature between −5 to 20° C., 0 to 15° C., or more preferably between 0° to 10° C. By maintaining the temperature low, the rate of matrix phase transition can be controlled as low as possible, for example, within a range between 2 minutes to 10 hours depending on the matrix concentration, preferably 30 minutes. The volume of the microspheres dispensed is controlled at between about 0.01 to 100 μl, 0.05 to 50 μl, 0.1 to 20 μl, 0.1 to 10 μl, 0.5±1 μl, or preferably about 2.5 μl. The diameter of the dispensed liquid droplets ranges from 0.5 mm to 3 mm, preferably 2 mm.

Sol-gel transition process of the liquid matrix is initiated by controlling the temperature, the pH and the ionic strength of the liquid environment at appropriate time. The temperature is raised from 4° C. to 10° C., 16° C., 25° C., 37° C. and preferably 37° C. The pH is raised from 2 to 5, 6, 7, 8, great than 8 and preferably 7. The speed of gelation of the gelling matrix can be slowed immediately after initiating the gelation by maintaining the temperature of the mixtures as low as 4° C. The speed of gelation of the gelling matrix can be increased immediately after dispensing the gelling matrix into droplets at the collecting unit by raising the temperature of the mixture to 37° C. or by increasing the ionic strength of the solution. The matrix components of the liquid droplets undergo phase transition to form cell-matrix microspheres for a period of time sufficient for phase transition to reach equilibrium, typically for about 10 to 30 minutes, 15 to 60 minutes, 0.5 to 5 hours, preferably 45 minutes.

The gelled droplets are detached or released from the collecting platform by gentle flushing with liquid such as culture medium and phosphate buffered saline, or immersing the platform in a liquid bath with gentle agitation, or other appropriate methods mile enough to retain the integrity of the soft microspheres. The microspheres are stabilized by collecting the cell-matrix microspheres from the collection platform with minimal mechanical disturbance; maintaining the microspheres free-floating in a first medium for an extended period of time until the size of the microspheres becomes substantially constant; and releasing the microspheres from the first medium. The microspheres can be maintained free-floating either by keeping in suspension in non-adhesive culture dish such as a Petri dish, or by culturing the microspheres in spinner flask or rotating vessel bioreactors. The microspheres can be maintained free-floating from 2 hours to 10 days, 12 hours to 8 days, or about 2 to 7 days, most preferably 3 days. The temperature can be maintained at about 25 to 45° C., 30 to 40° C., or about 37° C.

The size and mechanical strength of the microspheres can be controlled by at least one of the following parameters: cell density, collagen concentration, serum concentration, composition of the ECM, ratio of the first and optional second ECM, volume of the liquid droplets, and duration of the free-floating status of microspheres. The mechanical strength and size of the microspheres can be controlled by at least one of the parameters mentioned above. For example, the initial cell density or the cell number per microsphere can be controlled at a range between 1 to 2500, 1 to 1000, 1 to 500, or about 250 cells/microsphere; concentration of the first ECM can be controlled at a range between about 0.01 to 10.0 mg/ml, 0.1 to 5.0 mg/ml, 0.1 to 3.0 mg/ml, or about 0.5 mg/ml; the ratio of the first ECM to the second ECM can ranged from 1:10 to 10:1, 1:5 to 5:1, 1:2 to 2:1, or about 1:1; the serum concentration can range from 0.1% to 50%, 0.5 to 30%, 1 to 25%, 5% to 15%, or about 10%. Increasing cell density, decreasing matrix concentration or decreasing volume of liquid droplets decreases size and increases stability of cell-matrix microspheres.

The size of the microspheres can be precisely controlled by multiple parameters including, but are not limited to, the initial cell density or the cell number per microsphere, ranging from 1 to 2500 preferably 250 cells per microspheres; the concentration of the collagen ranging from 0.1 to 8.0 preferably 0.5 mg/ml; the serum concentration ranging from 2 to 20 preferably 10%; and the ratio between different matrix components such as collagen to GAGs ranging from 10:1 to 1:10 preferably 1:1.

Formulation parameters of cell-matrix microspheres can be optimized for better differentiation of encapsulated stem cells. For example, collagen-mesenchymal stem cells (MSC) microspheres can be prepared with different parameters such as cell density and collagen concentration. Parameters can be varied to give optimized differentiation outcomes such as GAGs production. Cell density between $1\times10^4$ to $1\times10^7$ cells per ml, preferably $5\times10^5$ cells per ml, can be used. Increasing cell density favors differentiation of human MSCs inside the microspheres into chondrocyte-like cells. Collagen concentration between 0.1 to 10 mg/ml, preferably 2 mg/ml, can be used. Increasing collagen concentration favors differentiation of human MSCs inside the microspheres into chondrocyte-like cells. Therefore these parameters can be optimized to give the best differentiation outcome during tissue regeneration.

In a preferred embodiment, the mechanical strength of the microspheres is controlled by controlling initial cell density or the cell number per microsphere, ranging from 1 to 2500 preferably 250 cells per microsphere; the initial concentration of the collagen matrix ranging from 0.1 to 8.0 preferably 0.5 mg/ml; the serum concentration ranging from 2 to 20 preferably 10%; the ratio between different matrix components such as collagen to GAGs ranging from 10:1 to 1:10, preferably 1:1; and the duration of the free-floating incubation ranging from 2 hours to 14 days, preferably 48 hours. Increasing cell density, decreasing matrix concentration and decreasing volume of liquid droplets dispensed, decreasing GAGs composition, increasing serum concentration and an increasing free-floating incubation time result in an increasing mechanical strength of microspheres obtained.

FIG. 1 shows a schematic drawing of a system 101 for producing the cell-matrix microspheres. The system 101 comprises a dispensing unit 100, which consists of a manual or automatic dispenser 102, a control unit 104 controlling the volume of the dispensing liquid, the speed of dispensing and X-Y position of the dispenser, and a cooling unit 106 (or ice chamber) accommodating the dispensing unit 100 at around 4° C. The system also includes a collecting unit 108, which consists of a scalable collecting platform 110 with non-adhering surface, a moving X-Y-Z stage 112 to which the collecting platform is mounted, a plate control unit 114 controlling the speed, frequency and direction of movement of the moving stage. The system may be manual or automatic, custom-made, or modified from commercially available instruments such as liquid handlers.

The method of forming microspheres via the system 101 comprises dispensing small liquid droplets such as 0.5 μl of mixtures containing the cells, the aqueous media and the liquid matrix, mixed in the right order of sequence and timing. The rate of matrix phase transition can be controlled by adjusting the temperature of the dispensing chamber side and is maintained slow by keeping the temperature low at the dispensing side. The diameter of the droplets range from 0.5 mm to 3 mm, preferably 2 mm. The liquid droplets collected at the collection platform are allowed to gel at 37° C. for sufficiently long to form the solid cell-matrix microspheres. The microspheres are released from the collection platform and maintained free-floating in culture conditions until stable microspheres are formed.

FIG. 2 shows a method of producing cell-matrix microspheres with controllable size and mechanical strength. The size and mechanical strength of the microspheres are controlled by multiple parameters including, but not limited to, the volume of cell-matrix mixture, the cell density or cell number per microsphere, the matrix density, the ratio of different matrix composition, the serum concentration, the volume of the liquid droplets dispensed and the duration of free floating incubation of the cell-matrix microspheres.

The method comprises Step 200: maintaining the gelled cell-matrix microspheres free floating or in suspension in static non-adhesive culture vessels, such as those for bacterial culture, or in spinning or rotating culture vessels, after releasing or detaching them from the non-adhesive collection platform 110, for sufficiently long period of time, ranging from 2 hours to 14 days, preferably 72 hours. Step 202: collecting the microspheres by flushing the microspheres with a medium on the collection platform 110. Step 203 involves allowing the microspheres to maintain for a period of time. Step 204: Examine the size of the microspheres until equilibrium is reached, i.e., the size of microspheres become constant. Step 206: collect the mechanically stable microspheres for injection or implantation or 3D cultures.

The duration of free floating depends on the rate of the cell-matrix interaction before reaching equilibrium where the size of the microspheres becomes constant. The rate of interaction is thus cell type and matrix type dependent. The diameter of the cell-matrix microspheres at equilibrium should be appropriate for in vivo therapeutic injection, ranging from 50 to 800 microns, preferably 300 microns.

IV. Method for Modifying Cell Behavior after Formation of Cell-Matrix Microspheres Cell migration from microspheres can be manipulated by providing a mechanical support to the microspheres by plating them onto a solid substratum of culture dishes or placing them into a gelling matrix or onto a gelled matrix; plating the microspheres into a culture dish or gelling matrix or onto gelled matrix wherein each microsphere is kept at a distance from each other; adding a second medium into the culture system for holding the microspheres; allowing cells to migrate out from the microspheres for a period of time; and releasing the microspheres from the attached substratum and the second medium. The microspheres are typically held in the culture system for a period of time before the second medium is added, for example, 30, 60, 90, or 120 minutes, preferably 60 minutes. The steps can be repeated several times to allow full migration of the cells. For example, the steps can be repeated 3, 5, 7, and preferably 10 times. The period of time for cell migration can range from 2, 4, 12, 48 hours to 12 days, preferably about 3 days. The cells that migrate out from the microspheres are allowed to grow for a period of time and can be harvested for future use or re-encapsulated. The culture system can be a 2D or 3D environment. The medium is preferably DMEM, DMEM-LG, MEM, or RPMI.

V. The Cell-Matrix Microspheres

The cell-matrix microspheres produced are mechanically stable and able to resist shear stress produced during rapid injection at a flow rate of as high as 20 ml/min, are able to survive mechanical manipulation such as picking up and down by forceps, and are able to survive turbulence produced during vortexing at maximal speed.

The collagen and other matrix provide the natural microenvironment stimulating growth of the cells, protect the cells from enzymatic digestion at the local hostile environment upon injection or implantation, immobilize soluble reagents, stimulating growth and differentiation if necessary, and the adhesive cell-matrix microspheres easily fuse together with the host tissue and fill any irregular gaps with the host tissue, therefore filling the tissue defects. The cell-matrix microspheres are permeable to free exchange of nutrients and metabolites. According to the rules of mass transfer in 3D tissue-like structures, the dimension of tissue-like structure is limited (Muschler, et al., *J. Bone Joint Surg. Am.*, 86-A(7): 1541-58 (2004)). While in the 3D cell-microsphere system, the size of the microspheres can be always controlled to as small as 100-300 microns, which is the suitable dimension of 3D structures with sufficient nutrient exchange. Another factor affecting the size of the microsphere is the matrix concentration. A higher concentration results in a stiffer matrix and therefore the traction force generated as the cells interact with the low concentration gelling matrix is not sufficient to produce a large extent of volume reduction. In addition, the encapsulated cells are able to migrate out the microspheres to integrate with the host tissue or grow rapidly when there is a close contact between the microspheres and the attached environment such as the host tissue thus may promote implants-host integration and engraftment rate.

The cell-matrix microspheres can also be used to immobilize other therapeutic molecules, for example, factors inducing specific differentiation lineage such as Transforming Growth Factor (TGF) beta for chondrogenic differentiation, and anti-inflammatory drugs.

The method includes steps of controlling the amount of cells obtained and the speed of obtaining such number of cells in a predictable manner by factors including but are not limited to the plating density of the microspheres ranged from 0.5 to 500 preferably 5 microspheres per $cm^2$; cell density ranged from 1 to 2500 preferably 250 cells/microsphere; concentration of matrix such as collagen ranged from 0.1 to 5.0 preferably 0.5 mg/ml; collagen to GAGs ratio ranged from 1:10 to 10:1 preferably 1:1; serum concentration ranged from 2 to 20 preferably 10%. An increasing plating density, an increasing cell density with a decreasing matrix concentration, a decreasing collagen to GAGs ratio and an increasing serum concentration result in an increasing number of cells obtained and an increasing speed of obtaining such number of cells.

FIG. 3 shows a method of controlling the migration and growth of encapsulated cells. Step 300 involves probation of mechanically stable microspheres according to the steps described in FIG. 1 and FIG. 2. Step 301 involves providing a mechanical support for the microspheres to attach, in the absence of medium supplementation, for a period of time sufficient for attachment, 5 minutes to 60 minutes, half an hour to 6 hours, preferably 45 minutes, via Steps 302-304. Step 302 and 303 involves plating microspheres (302*a*) onto the solid substratum of a culture dish and a layer of collagen gel (303*a*), respectively. Step 304 involves suspending microspheres in a volume of gelling collagen matrix (304*a*) and cast the mixture into a culture dish for gelation by raising the temperature to 37° C. Step 305 involves adding full medium (305*a*) into the culture dishes without disturbing the attached microspheres. Step 306 involves allowing cell migration (306*b*) from the circumference of the microspheres for a period of time, from 12 hours to 3 days, from 2 days to 8 days, from 4 days to 14 days, preferably 3 days. Step 307 involves retrieval or releasing of the cell-matrix microspheres from the attached substratum by methods such as gentle flushing the substratum with full medium. Step 308 involved immediate supplementation of full medium to the culture dish where the migrated cells (308*a*) are allowed to continue to grow with regular medium change. Step 309 involves recycle of the detached microspheres for plating and cell outgrowths in steps 301-307 (not shown). The cells migrated can be harvested in Step 310 for future use.

The method includes providing attachment to the floating microspheres by plating the contracted cell-matrix microspheres onto an adhesive substratum such as culture dishes in the absence of medium for certain period of time ranging from 30 minutes to 12 hours, preferably 45 minutes, until attachment is achieved. The method also includes steps of replenishing the microspheres with sufficient medium without disturbing the attached microspheres.

The method includes steps of allowing cell outgrowth from the attached cell-matrix microspheres. The collagen matrix is permissive to cell migration. Together with the population pressure built up in the fully contracted cell-matrix microspheres, it results in cell outgrowth from the periphery of the attached microspheres onto the substratum or surrounding environment and the migrated cells proliferate. Cell outgrowth is induced for a certain period of time ranged from 12 hours to 14 days preferably 3 days.

The method includes removing the attachment of the cell-matrix microspheres when sufficient number of cells migrate out from the microspheres that the microspheres are surrounded with cell outgrowths. This occurs at 12 hours to 14 days, preferably 3 days. The step does not need enzymatic digestion such as trypsinization, which may change the surface marker and cellular activities, and without mechanical disruption of the microspheres; but simply by flushing the microspheres gently with medium or PBS or by picking up with forceps.

The cell-matrix microspheres are intact and are collected by sendimentation or mild centrifugation ranged from 800 to 2000 rpm preferably 1000 rpm.

The cell-matrix microspheres can be replated in new empty culture vessels multiple times, up to 10 platings depending on the microsphere size, cell density per microsphere, so as to provide large number of cells in the same passage without changing the cell growth and differentiation potential as well as surface markers.

The method can be used to provide cells on demand by maintaining the cell-matrix microspheres in suspension for at least one week if no cells are needed. The free-floating microspheres are provided with attachment in order to allow cell migration and outgrowth until confluence for future use when cells are needed. The method enables the constant supply of cells from the same passage in the cell-matrix microspheres by plating the microspheres for multiple times until the cell migration ceases. The migrated cells can be obtained at regular intervals, preferably daily, for a period of time ranging from 2 to 30 days preferably 10 days, that is the period of time necessary for building multi-layered heterogenous tissue-like structure including, but are not limited to, the IVD, GI tract and blood vessels.

The cell-matrix microspheres can be dissembled simply by enzymatic digestion specific to the matrix components of the microspheres, such as collagenase for collagen, chondroitinase for chondroitin sulfate GAGs. The single cell suspension can be used further.

The natural extracellular matrix materials such as collagen used to encapsulate cells provides a physiologically relevant microenvironment in 3D to the encapsulated cell by forming cell-matrix microspheres. The tissue-like matrix microenvironment imposed on the encapsulated cells constrains cell proliferation. As a result, the cells are temporarily controlled for proliferation and the cell number in 3D microspheres increases only slightly higher than 2 fold on day 4 while cells in traditional monolayer cultures increase over 20 fold for the same period of time. The proliferation index for cells in 3D microspheres is consistently lower than that in traditional monolayer culture at different time points and for different cell densities. This method presents a naturally occurring and externally applied control for proliferation that no genetic manipulation on cell metabolism is needed.

IV. Applications

A. Tissue Repair or Regeneration

The methods and cell matrix microspheres are useful for treatment of cardiovascular diseases such as repair of myocardial infarction, for neurological diseases such as spinal cord injury and for musculoskeletal diseases such as cartilage injury, disc degeneration and muscular dystrophy. Services or products associated with stem cell therapies can also use the method and cell matrix microspheres to culture stem cells in 3D or in combination with monolayer cultures, to produce stem cells in large quantity and with a request-by-demand approach without changing their identity, self-renewal and differentiation capacity.

The cell-matrix microspheres consisting of undifferentiated and viable cells can be injected or implanted, for example, for tissue repair or regeneration. The method includes the steps of sedimenting the microspheres for a period of time, preferably 10 minutes or centrifuging the microsphere suspensions mildly at a speed of 800-200 rpm, preferably 800 rpm, for a period of time, preferably 5 minutes; removing the excess supernatant; re-suspending the microspheres in a liquid for injection or implantation such as saline or medium or phosphate buffered saline or a low concentration hydrogel such as collagen gel with a known volume; adding the microsphere suspension to a container for injection or implantation such as a syringe with G18-G30 needles, preferably G27; and injecting or implanting the microspheres into defective tissues in animals or humans such as a skin wound or an injured cartilage.

In one embodiment, the method includes injecting or implanting the cell-matrix microspheres consisting of specifically differentiated and viable cells, wherein the matrix embeds these cells into defective tissues of animals or humans. The method comprises adding differentiation medium where chemical signals such as TGF-b is included in the microsphere suspensions for a period of time sufficient to induce chondrogenic differentiation of stem cells present in the microspheres into chondrogenic cells; allowing the microspheres with differentiated cells to sediment for a certain period of time, preferably 10 minutes, or centrifuging the microsphere suspensions mildly at a speed of 800-2000 rpm, preferably 800 rpm, for a period of time, preferably 5 minutes; removing the excess supernatant; re-suspending the microspheres in a liquid for injection or implantation such as saline or medium or phosphate buffered saline or a low concentration hydrogel such as collagen gel with a known volume; adding the microsphere suspension in the container for injection or implantation such as a syringe with G18-G30 needle, preferably G27; and injecting or implanting the microspheres into defective tissues in animals or humans such as a skin wound or an injured cartilage. The microspheres can be used for cell therapy via injection or implantation for disorders including, but are not limited to, those of the musculoskeletal, cardiovascular and neurological systems.

The cell-matrix microspheres can be used as long term sources for cells from the same passage without the need for cell splitting as conventionally used in both monolayer culture and seeding cells on 3D scaffolds such as using repeated enzymatic digestion and mechanical disruption.

B. Cell-Matrix Microspheres as BioReactors

Companies that provide services or products associated with 3D microcarriers in culture of cells, genetically modified or not, for production of therapeutic biomolecules such as but not limited to growth factors, can use the methods and compositions to produce self-assembled microcarriers that further enhance the yield of therapeutic molecules produced. Cell-matrix microspheres can be used for 3D cultures as traditional microcarrier cultures used in biotechnology and pharmaceutical industries. They can be cultured as suspensions so as to easily increase the bed volume and scale up the culture system. Comparing with traditional microcarrier cultures, the method provides several important advantages in enhancing efficiency and reducing costs. Cells are immobilized within the gelling matrix at almost 100% encapsulation efficiency that almost all cells can be encapsulated. This encapsulation procedure takes only 30-60 minutes in static culture conditions. On the other hand, traditional microcarrier culture system needs a time-consuming and inefficient cell binding procedure to allow cells to bind to the surface of the pre-fabricated microcarriers in suspension. In order to increase the efficiency of cell binding to the pre-made microcarriers, complicated culture vessel design such as rotating vessel bioreactors, perfused bioreactors, spinning flasks and other methods such as constant agitation are needed. This cell binding step sometime may take more than 1 week. Since the method eliminates the necessity of these complicated and time-consuming steps, it presents a more efficient and less costly 3D culture method. Second, the microencapsulation system combines the formation of the microspheres and the immobilization of cells in a matrix system into one step. This significantly reduces the cost and saves time. Moreover, it eliminates the necessity of fabricating microcarriers separately that dramatically reduces the cost of the system because technologically demanding steps for fabrication of microcarriers such as phase separation, solvent evaporation, chemical crosslinking can be avoided. Third, the microencapsulation system is conducted in physiologically relevant temperature and conditions that assures high cell viability. On the other hand, residues of organic solvents and toxic chemical crosslinking reagent such as glutaraldehyde used during fabrication process of microcarriers may compromise cell viability.

The cell matrix microspheres are also useful for 3D cultures. These have numerous advantages over the existing microcarrier systems. The system can be used to culture protein-secreting cells in physiologically relevant microenvironment with significantly increased protein productivity via matrix-induced proliferation control as compared to monolayer cultures with unrestricted proliferation.

The productivity in 3D microspheres increases when the microspheres are cultured in low serum concentrations such as 2%. This indicates that the culture system can be maintained at low serum concentrations and the downstream purification of proteins can be simplified. The cells are cultured in culture vessels or bioreactors with or without constant agitation or spinning or rotation or perfusion.

The secreted proteins in the culture medium are harvested with replacement at regular periods ranging from 1 day to 10 days, preferably 2 days, before reaching the maximal cell density inside the microspheres, for a period of time after microsphere suspension culture, ranging from 7 day to 3 months preferably 14 days. Wider windows for protein production can be achieved by encapsulating the cells in suboptimal concentrations in the liquid matrix, ranging from $1\times10^4$ to $1\times10^7$ cells/ml, preferably at $1\times10^5$ cells/ml. The productivity of cells is significantly increased when cells proliferation inside the matrix microspheres is controlled. This window can be maintained for at least 2 weeks, much longer than the window with enhanced productivity in other controlled proliferation strategies. Unlike other proliferation control technologies, this method provides a temporary and reversible control for proliferation by encapsulating the cells in natural extracellular matrix materials at appropriate concentrations and time.

Similar to 2D culture without the matrix microspheres, the cell number increases linearly during the log phase. During this phase, total protein production increased linearly with cell number and the productivity of specific proteins is reduced. This may be due to the fact that more energy is channeled to reproduction rather than protein production. Specific proteins produced during this phase can also be harvested. Cells will reach a maximal or optimal density due to the space limitation and nutrients competition, and the proliferation rate of the cells will be reduced. This is usually accompanied by an increase in protein production. However, during this phase, cell apoptosis and death may be induced and the release of intracellular contents may degrade the secreted products. It is therefore advantageous to harvest the secreted proteins at appropriate time points during the optimization. Unlike other systems, this method allows separation of high protein productivity and rapid proliferation. This protein production phase is prior to and accompanied by a log proliferation phase. This system is therefore sustainable and typically ends with dramatically increased cell numbers.

Efficiency and cost reduction of the culture system can be achieved by recycling the encapsulated cells after reaching the optimal cell density after a period of time ranging from 2 weeks to 3 months, preferably one month, via re-encapsulation. It is economically efficient because the protein harvest can start well before active proliferation phase while the output of the system includes not only the specific proteins produced but also increased cell numbers with high viability. Moreover, the cycle can be restarted by enzymatically releasing the cells and re-encapsulating into new matrix microspheres so that the cycle of matrix-induced proliferation control with high protein productivity and the subsequent active cell proliferation in 3D microspheres can be initiated again.

Another advantage of this system is that, unlike traditional proliferation controlling technologies such as nutrients deprivation and over-expression of tumor suppressor genes, to control cell metabolism and to induce cell apoptosis or death, where high cell viability (almost 100%) is always maintained at different time points, with different cell densities and serum concentrations, proliferation of cells can be controlled directly, increasing protein productivity. In the example using GDNF-secreting HEK293 cells, the productivity of cells in 3D microspheres is always higher (ranging from 3 to 67 fold) than that from the monolayer cultures at different time points, with different cell densities and at different serum concentrations.

EXAMPLES

The present invention will be further understood by reference to the following non-limiting examples.

Example 1

Production of hMSC-Collagen Microspheres

Rat-tail collagen solution type I in acetic acid, which mainly consists of triple helical monomers, was neutralized by NaOH and diluted into a final concentration of 0.5 mg/ml. All procedures were done in an ice-bath to prevent collagen gel formation. Human bone marrow derived mesenchymal stem cells (MSCs) in full medium, DMEM-LG with 10% FBS and 1% P/S, were suspended thoroughly in the neutralized collagen solution as soon as possible. A dispenser was then loaded with the ice-cold cell mixture and a small volume of 2.5 µl was dispensed at a time onto a bacterial culture dish covered with UV-irradiated parafilm. To prevent air-bubble formation in the liquid droplets, the dispenser was moved upwards or the collection platform downwards after dispensing the liquid droplets. The liquid droplets were thermally induced to reconstitute into a gel meshwork of organized collagen fibrils, interacting with the encapsulated cells, to form solid microspheres by incubating in a 37° C. incubator for 1 hr. The cell-matrix microspheres formed were collected into a full medium containing bath with non-adherent substratum by gently flushing the parafilm with medium.

Example 2

Production of Mechanically Stable Cell-Matrix Microspheres and Controlling Parameters of the Microsphere Size Materials and Methods Following the steps shown in FIG. 2, rat-tail collagen solution type I was neutralized and diluted into different concentrations (0.5, 1.0, 2.0 and 3.0 mg/ml) in the presence of different concentrations ($2 \times 10^4$, $1 \times 10^5$ and $5 \times 10^5$ cells/ml) of human bone marrow derived MSCs in DMEM medium with 10% FBS as described in Example 1. The cell-matrix microspheres were collected into a DMEM medium containing bacterial culture dish. The collected microspheres were maintained at their free-floating state in the culture vessel at 37° C. for 2 to 7 days until the equilibrium is reached as characterized by a constant microsphere size.

Results

Figure 4A:
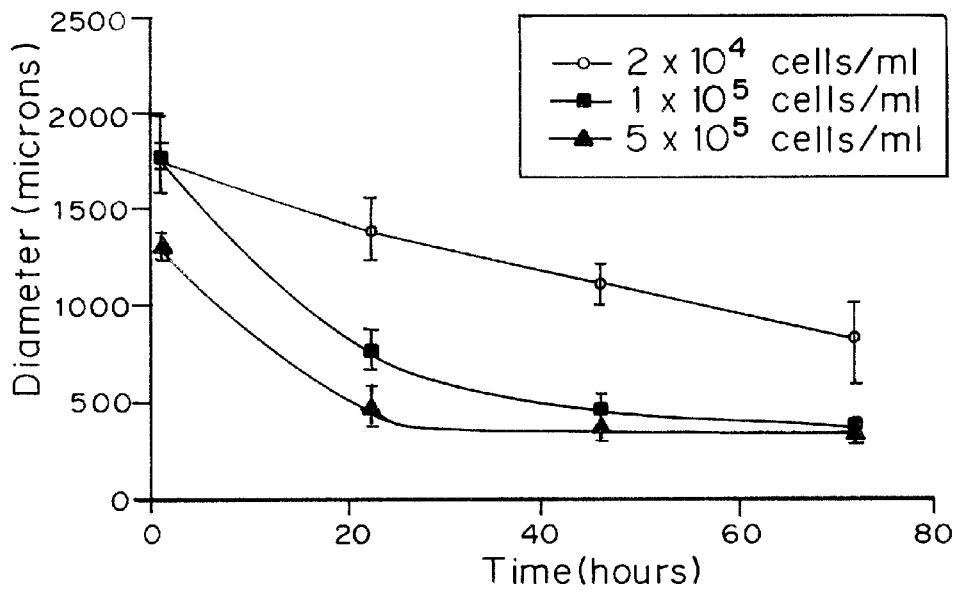
FIGS. 4A, 4B and 4C are graphs showing changes in diameters of hMSC-collagen microspheres (microns) against time (hours) as functions of cell density (FIG. 4A), collagen concentration (FIG. 4B) and droplet volume (FIG. 4C).
Figure 4B:
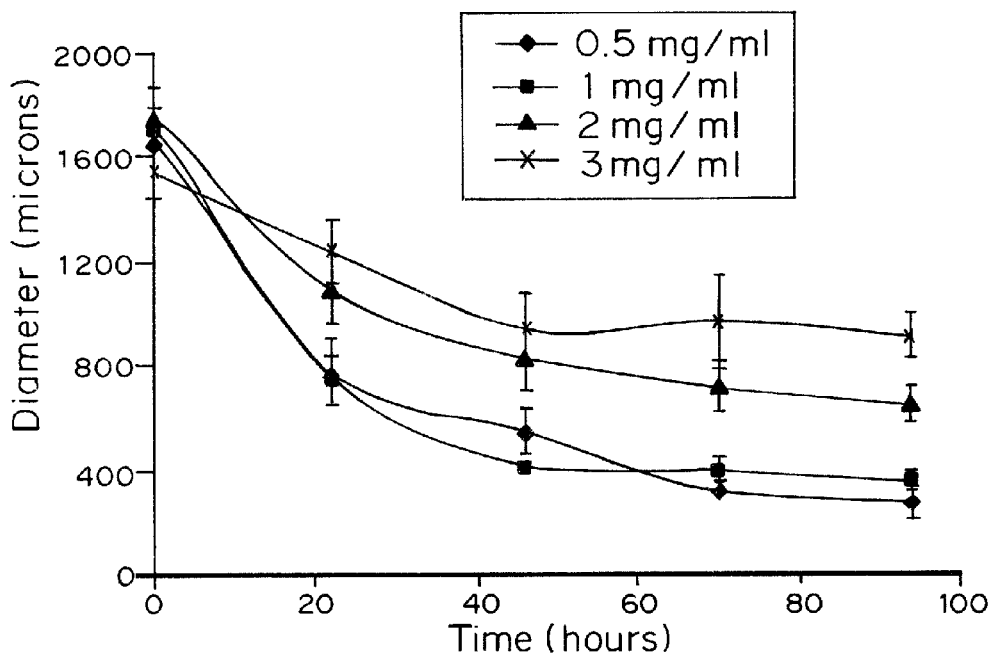
Figure 4C:
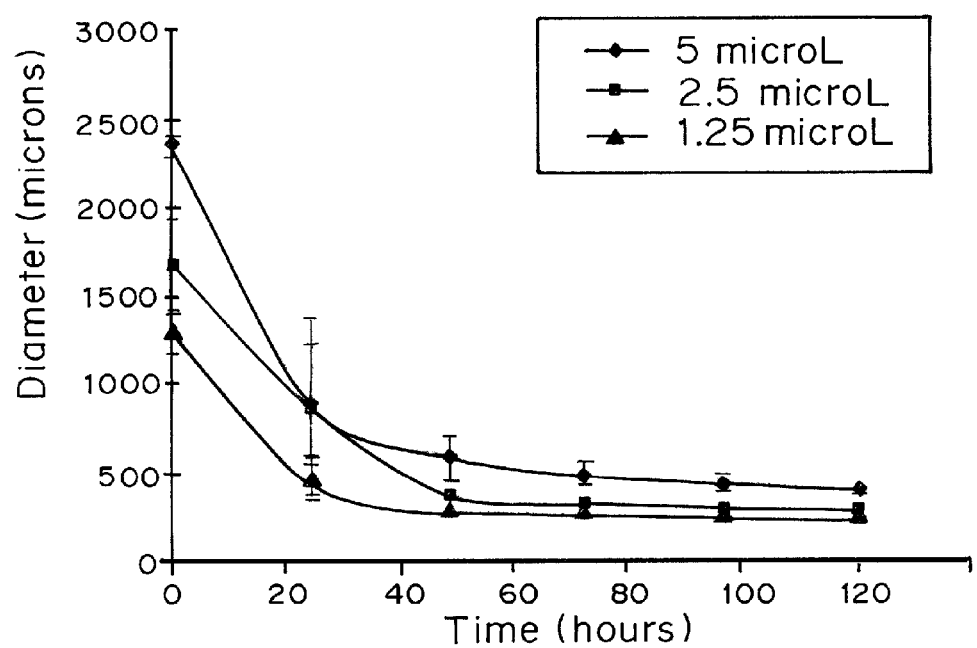

The temporal morphological change of the cell-matrix microspheres with different cell densities and collagen matrix densities were recorded. Microspheres at day 0 showed individual cells embedding in the collagen materials and the microspheres were still transparent. Microspheres at higher cell densities such as $1 \times 10^5$ and $5 \times 10^5$ cells/ml and lower collagen matrix densities of 0.5, 1.0 and 2.0 mg/ml contract as time goes by and become more opaque and dense. This indicates that hMSCs are reorganizing the matrix to form a tighter matrix in the microspheres. Microspheres at lower cell density ($2 \times 10^4$ cells/ml) took much longer time to contract to a constant size while microspheres with higher collagen matrix density, 3.0 mg/ml, showed so little contraction that the matrix appears transparent. The extent of hMSC-induced collagen microspheres contraction was directly proportional to the cell density, collagen concentration and droplet volume (FIGS. 4A, 4B, and 4C, respectively), establishing that that these parameters can be used to control the final size of the microspheres. The hMSC-collagen microspheres, after reaching the equilibrium, can be mechanically manipulated by forceps and are resistant to the shear stress and turbulence generated during pipetting up and down at rapid rate such as 20 ml/min or even vortexed with maximal speed. As a result, these microspheres are mechanically stable enough to resist shear stress generated during microsyringe injection and are ready for injection and implantation for cell therapy and tissue engineering purposes.

Example 3

Controlling the Growth Rate of Encapsulated hMSCs Inside the Collagen Microspheres Materials and Methods hMSCs were isolated from bone marrow aspirates from donors with informed consent in compliance with the Institute human ethics regulations. hMSCs were cultured as described by Li et al. 2004. Cells harvested from passage 2 and 3 by traditional monolayer culture were cryopreserved and used for production of cell-matrix microspheres with different collagen density: 0.5 and 2 mg/ml. Fully contracted mechanically stable hMSCs-collagen microspheres were obtained as described in Examples 1 and 2. These microspheres were incubated with 2 µM Calcein AM and 4 µM Ethidium homodimer-1 for 45 minutes for simultaneous staining of live and dead cells. Stained microspheres were fixed in 4% paraformaldehyde for 1 hour and examined using a laser confocal scanning microscope for stacked images. In a separate experiment, microspheres, with 100 microspheres per plate in triplicates, were cultured in full medium for 10 hours, 3, 6 and 9 days. At the end of incubation, the microspheres were digested with bacterial collagenase at 100 U/ml for 45-80 minutes at 37° C. followed by digestion with 0.05% Trypsin/EDTA for 5 minutes. The single cell suspension obtained was counted for cell number and viability.

Results

Figure 5A:
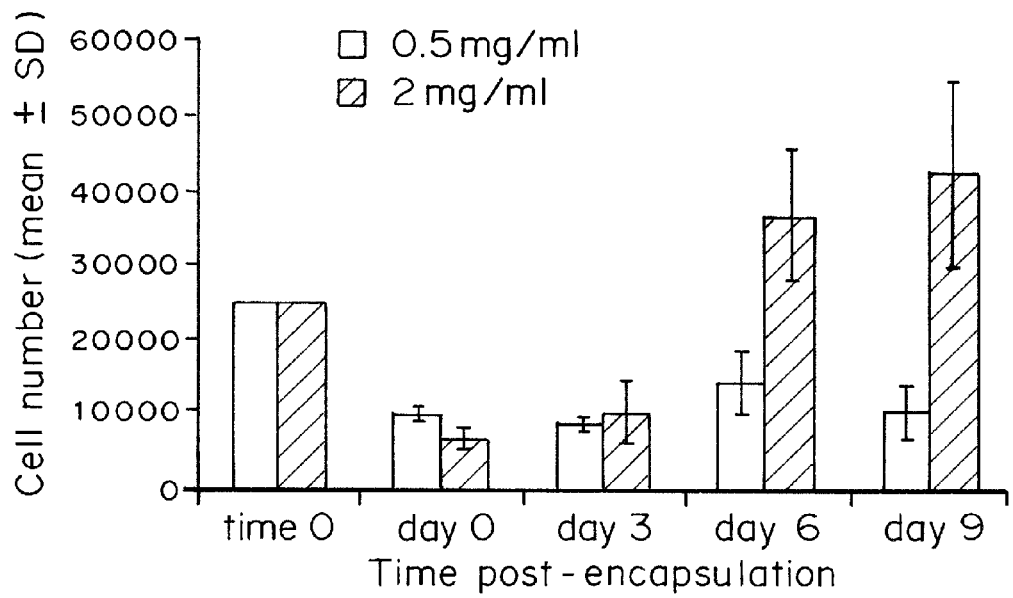
FIGS. 5A and 5B are graphs of the cell number (FIG. 5A) and viability of encapsulated hMSCs, cell number over time post-encapsulation (days). All data are presented as mean+/−SD.
Figure 5B:
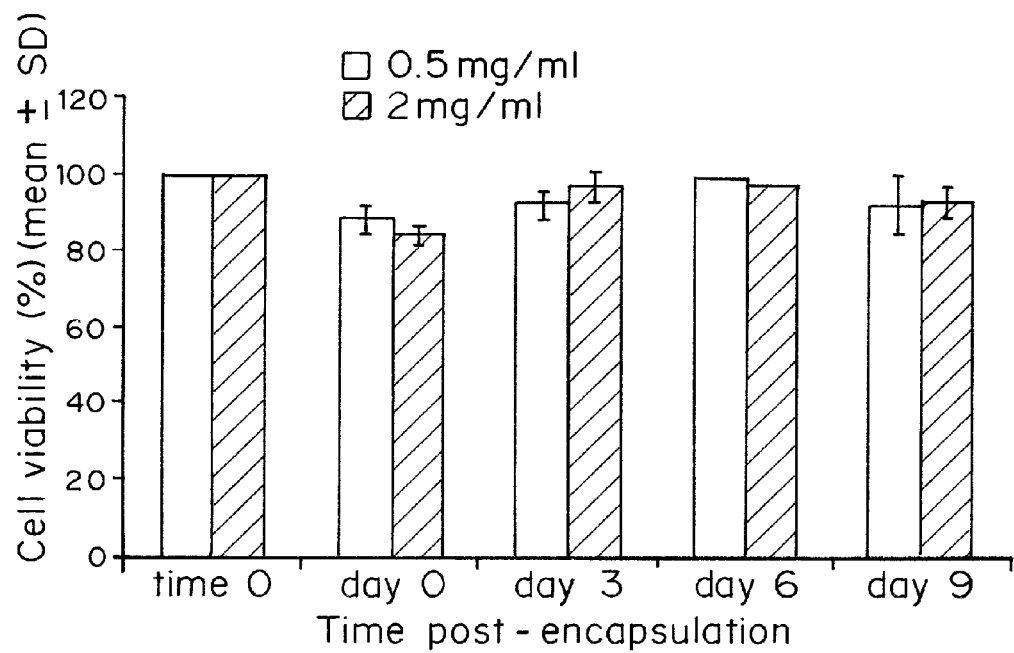

Both live and dead cells were found initially after microencapsulation. After 3 days, most cells in microspheres with lower collagen concentrations were alive while dead cells could be found in microspheres with higher collagen concentrations. All live cells exhibited elongated morphology. At day 6, cells were more elongated and achieved cell-to-cell contact. In microspheres with lower collagen concentrations, cells were distributed throughout the matrix while those with 3 mg collagen/ml, had more cells aligned at the circumference. Growth of the microencapsulated cells was collagen concentration dependent, as shown by FIG. 5A. At 8 hours post-encapsulation, the cell number fell to approximately 40% of those initially microencapsulated in both concentrations. There was only slight increase in cell number after day 6 for the 0.5 mg/ml group but a rapid increase in cell number was observed in the 2 mg/ml group. Two-way ANOVA showed that both time and collagen concentration significantly affected the cell number (p<0.001). Bonferroni's post-hoc tests showed significant different between day 6 or 9 and earlier time points (p<0.001). A significant reduction in cell viability (p<=0.033) was found at 8 hours but not thereafter (p=0.959), as shown by FIG. 5B.

Example 4

Controlling the Migration and Growth of Encapsulated hMSCs from Collagen Microcapsules Materials and Methods Free-floating hMSC-collagen microspheres with cell densities of $2 \times 10^4$, $1 \times 10^5$ or $5 \times 10^5$ cells/ml were transferred into 100 mm diameter tissue culture plates at 3 days post-encapsulation, at plating densities of 63, 125 or 250 microspheres per plate corresponding to 0.64, 1.59 and 3.18 microspheres/$cm^2$. The microspheres were allowed to attach to the culture plate for 1 hours after aspiration of excess medium and supplemented with full medium. At 72 hours, the microspheres were detached from the culture plates by gently flushing with full medium, allowed to sediment and replated in new culture plates several times until cell out-growing ceased. In separate experiment, microspheres were seeded on collagen gel at 0.5 mg/ml to evaluate whether cells would migrate into soft substratum. Cells growing out from the microspheres after different platings were cultured for 12 days with regular medium change while their morphology recorded at 3, 38 and 154 hrs. The outgrowing cells from 250 microspheres were trypsinzed for cell count for comparison with the conventional monolayer cultures seeded with the same initial cell number.

Results

Figure 6A:
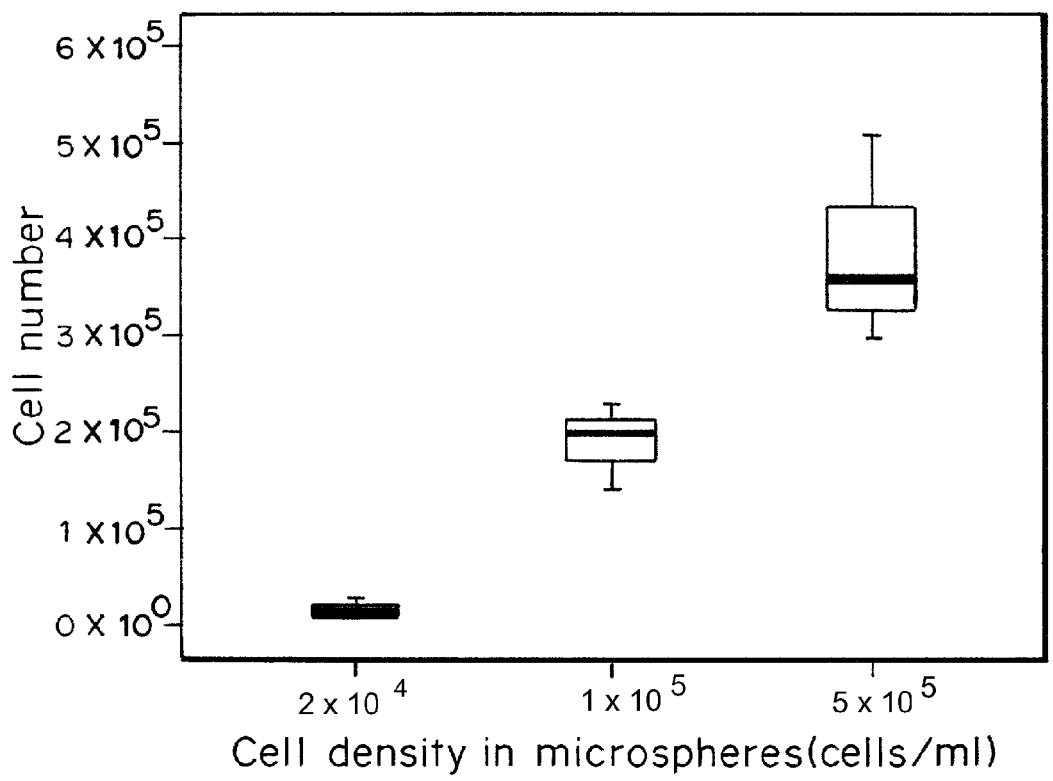
FIGS. 6A-6D are graphs showing cell number versus cell density in microspheres, cells/ml, (FIG. 6A), cell number versus plating density, microspheres/cm$^2$ (FIG. 6B), cell number, 95% CI versus monoplating, 3D first plating, 3D second plating, 3D third plating, and 3D fourth plating, (FIG. 6C), and microspheres number for the first, second, third and fourth plating (FIG. 6D). The central line is the median; the upper most and lower most bar are the $2.5^{th}$ and $97.5^{th}$ percentile of data, respectively; the upper and lower limit of the box are the $25^{th}$ and $75^{th}$ percentile of data, respectively, showing showed the number of outgrowing cells as functions of cell density (FIG. 6A) and plating density (FIG. 6B); Error bar plot (data are presented as mean+/−95% Confidence Interval) compared the cell number between monolayer culture and 3D microspheres (FIG. 6C); Box plot showed the number of microspheres at different platings (FIG. 6D).
Figure 6B:
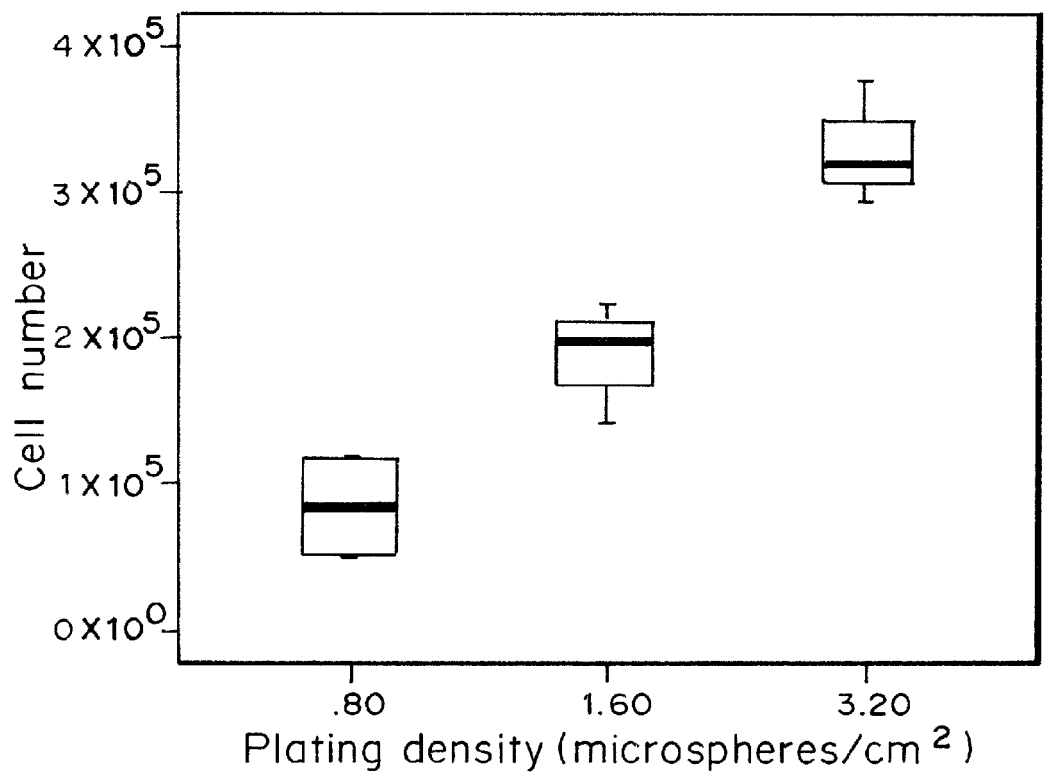
Figure 6C:
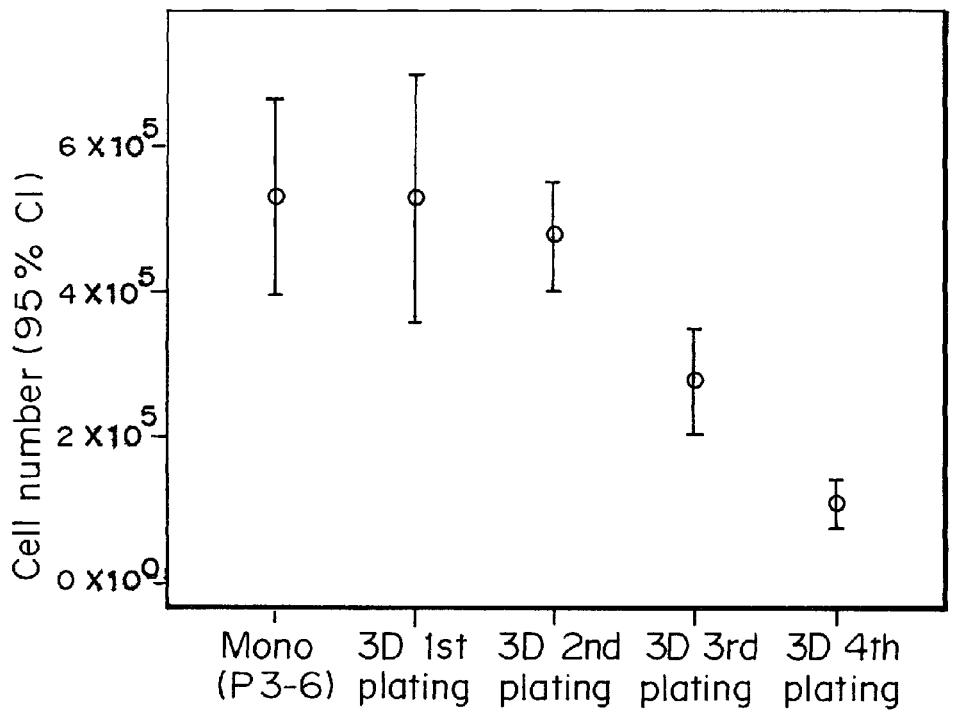
Figure 6D:
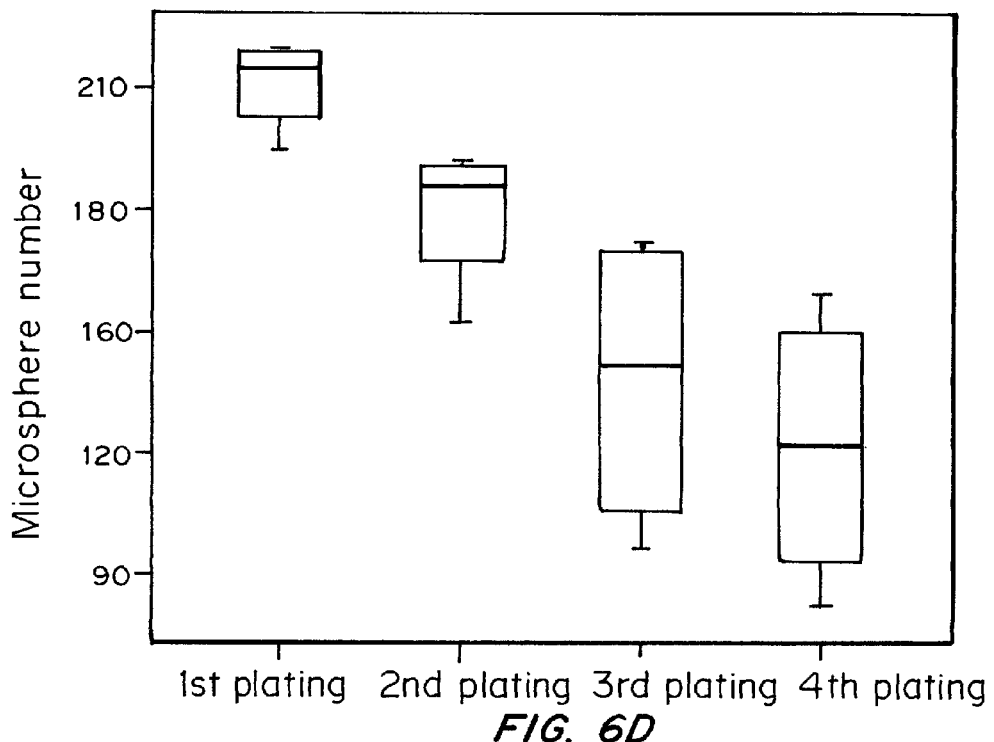

There was no cell migration immediately after plating of microsphere. At 38 hours, cells migrated out and formed clusters. After detaching the microspheres at 72 hours, the outgrowing cells grew to form large colonies. These cells were homogeneously small and elongated and can be cryopreserved for future use such as cell-based assays, frozen stocks, re-encapsulation and fabricating tissue-like structures. The morphology of the outgrowing hMSCs was maintained even after 10 platings and the morphology simulated that from the early passages of the monolayer culture. By contrast, scarce out-growing cells were noted in microspheres with low cell density. The number of out-growing cells increased linearly when cell density (FIG. 6A) and microsphere plating density (FIG. 6B) increased. Kruskal Wallis tests showed significant differences between groups (p=0.044). The detached microspheres could be replated several times without enzymatic digestion. Microspheres encapsulated with 250 cells could be plated for at least three times while those with 500 cells for at least six times. Moreover, the cell number obtained from early platings of microspheres was comparable with monolayer cultures (FIG. 6C) while a significant decrease (p<=0.018) in later platings was noted. This was related to the significant decrease (p=0.009) in microsphere number (FIG. 6D) due to aggregation and disintegration. Microencapsulated hMSCs were also able to migrate into soft collagen gel. The viability of cells from different platings showed no difference. Microspheres aggregation and disintegration can be observed after 72 hours post-attachment. Outgrowing cells at 24 hours post-attachment penetrated into the collagen gel.

Example 5

Maintenance of the Surface Marker of hMSCs Outgrowing from the Microspheres after Multiple Platings Materials and Methods hMSCs migrated out from microspheres after 10 platings were trypsinized with 0.05% trypsin in EDTA for 6-9 minutes and then fixed and labeled with antibodies against surface markers including CD34, CD14, CD29, CD105, CD45 and HLA. Flow cytometry was performed using appropriate isotype controls as described previously (Li et al. 2004).

Results hMSCs showed the same surface markers panels, negative for CD14, CD34 and CD45, positive for CD105, CD29 and HLA-A,B,C, as that obtained from P1 of monolayer cultures. This indicates that the identity of the hMSCs was not changed even after 10 cycles of plating and replating of the hMSC-collagen microspheres. Since these cells are from a single aliquot of monolayer cultures of the same passage and these plating cycles can be repeated using another aliquot or aliquots from another passage from the monolayer culture, by combining this 3D culture system and traditional monolayer cultures, long term storage and rich sources for cells, which are necessary for cell-based assays and fabrication of tissue-like structures in tissue engineering can be achieved.

Example 6

Maintenance of the Self-Renewal Capacity of hMSCs Outgrowing from the Microspheres after Multiple Platings Materials and Methods A colony formation assay was used to characterize the self-renewal potential of hMSCs obtained from the 3D and the monolayer cultures. hMSCs obtained from the $3^{rd}$-$5^{th}$ passages of the traditional monolayer culture and from the $1^{st}$-$5^{th}$ platings of the 3D culture were seeded at very low density at 250 cells per 100 mm diameter culture plate in triplicates and were cultured for 14 days with regular medium replenishment. The colonies formed were stained and fixed with 5% crystal violet (Sigma) in methanol for 10 minutes and rinsed with distilled water twice. The number of colonies with diameter greater than 2 mm was counted and the single-cell-derived colony forming efficiency was calculated as the percentage of colony formed of all cells seeded.

Results

Figure 7:
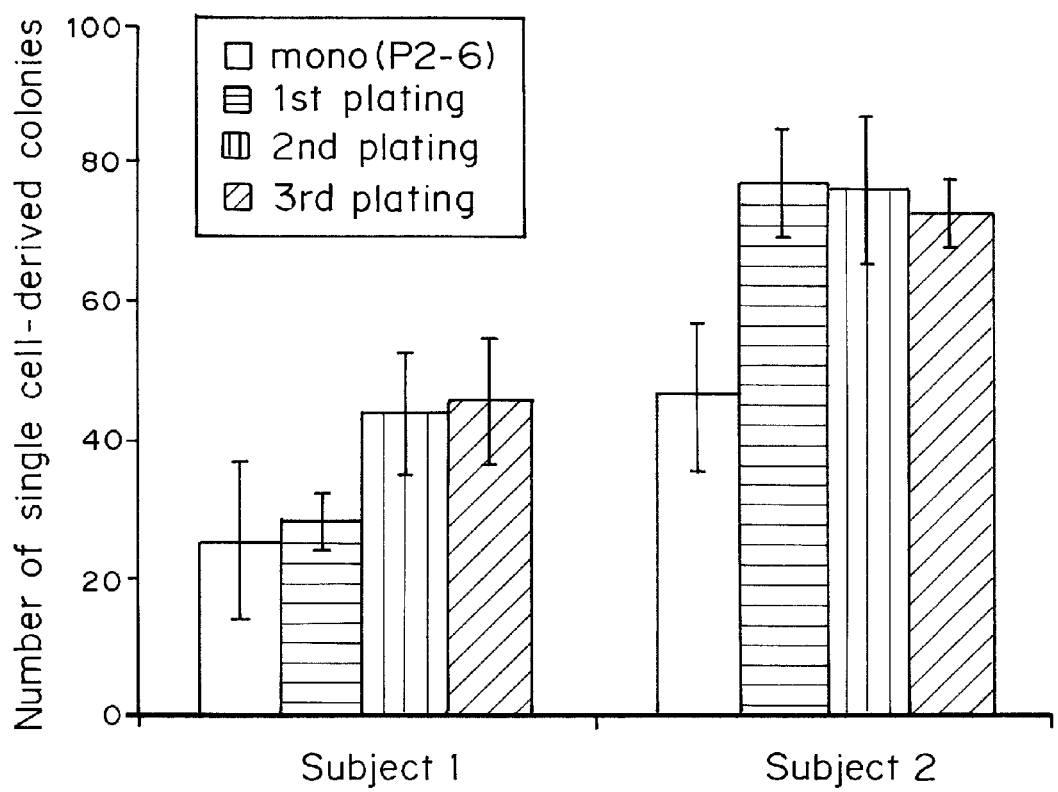
FIG. 7 is a bar chart showing the number of single-cell derived colonies formed from cell outgrowths from the hMSC-collagen microspheres, in two subjects, comparing mono, first, second and third platings.

Self-renewal capacity of the cell outgrowths from the microspheres after multiple platings was comparable with that obtained from traditional monolayer cultures, as shown by FIG. 7. One-way ANOVA showed that there was no statistically significant difference in the number of single-cell-derived-colonies in all groups (p>0.05).

Example 7

Maintenance of the Multiple Differentiation Potential of hMSCs Outgrowing from the Microspheres after Multiple Platings Materials and Methods Multiple Differentiation Potential of Cell Outgrowths Differentiation assays for chondrogenesis, oesteogenesis and adipogenesis were performed to investigate whether hMSCs obtained from the 3D microspheres still retain the multiple differentiation potential according to standard protocols in previous reports (Pittenger et al., *Science*, 284(5411):143-7 (1999); Okamoto, et al., *Biochem. Biophys. Res. Commun.*, 295(2):354-61 (2002); Romanov, et al., *Bull. Exp. Biol. Med.*, 140(1):138-43 (2005)). Cells obtained from the passage 2 of monolayer culture and the $3^{rd}$ and $10^{th}$ platings of the 3D cultures were used.

Chondrogenesis

Aliquots of $2 \times 10^5$ cells in a 15 ml centrifuge tube (Falcon) were centrifuged at 800 rpm for 5 minutes at room temperature. The pellet was resuspended in chondrogenic differentiation induction medium, which was defined as DMEM high glucose, supplemented with 10 ng/ml recombinant human transforming growth factor beta 3 (hrTGF-β3), 100 nM dexamethasone, 6 mg/ml insulin, 100 mM ascorbic acid 2-phosphate, 1 mM sodium pyruvate, 6 mg/ml transferring, 0.35 mM praline and 1.25 mg/ml bovine serum albumin. Cells were centrifuged as pellet again and maintained for 3 weeks with regular induction medium replacement every 2 days. At the end of the incubation, pellets were fixed and processed for 5 μM thick paraffin sections for Alcian blue staining.

Osteogenesis

Full medium was further supplemented with 100 nM dexamethasone, 50 μM ascorbic acid 2-phosphate, and 10 mM β-glycerophosphate as the oesteogenic differentiation induction medium. hMSCs were seeded at $3 \times 10^3$ cells/cm$^2$ in 4 or 6 well plates in duplicates or triplicates and were maintained in the differentiation induction medium for 3 weeks with regular medium replacement every 3 days. At the end of the incubation, cells were rinsed with PBS, fixed with 10% buffered formalin for 10 minutes at room temperature and stained with 5% silver nitrate (Nakarai Tesque, Kyoto, Japan) for von Kossa staining.

Adipogenesis

Adipogenic differentiation induction medium was prepared by supplementing the full medium with 1 μM desamethasone, 0.2 mM indomethacin, 10 μg/ml insulin and 0.5 mM 3-isobutyl-1-methylxanthine while the maintenance medium was prepared by supplementing the full medium with only 10 μg/ml insulin. hMSCs were seeded at $2 \times 10^4$ cells/cm$^2$ in 4 or 6 well plates in duplicates or triplicates in full medium until confluence. Adipogenic differentiation induction medium was added for 3 days followed by 2 days in maintenance medium and three induction/maintenance cycles were performed. Cells were rinsed, fixed and then stained with 0.3% Oil-Red-O (Nakarai) for oil droplets staining.

Results

Multiple differentiation potential of hMSCs was maintained after multiple cycles of plating. Cell outgrowths obtained from the microspheres after $3^{rd}$ and $11^{th}$ platings were still able to differentiate into osteoblasts, adipocytes and chondrocytes. This was demonstrated by the positive staining in von Kossa, Oil Red O and Alcian blue stainings for calcium deposits, oil droplets and proteoglycans, respectively.

Example 8

Chondrogenic Differentiation of hMSCs in Collagen Microspheres

Materials and Methods hMSCs at a final concentration of $5 \times 10^6$ cells/ml was suspended in 100 μl of neutralized collagen solution (2 mg/ml). Microspheres so prepared were incubated in chondrogenic differentiation medium for 3 weeks as described in Example 7. The differentiated microspheres were stained for cartilage-specific matrix markers as described in Example 7.

Results

Cartilage micro-tissues could be formed as the microencapsulated hMSCs were able to be chondrogenically differentiated into chondrocyte-like cells with typical round morphology. The differentiated cells lost their ability to migrate and produced cartilage-specific extracellular matrix as shown by the positive staining for glycosaminoglycans, aggrecan and type II collagen.

Example 9

In Vivo Subcutaneous Implantation of Collagen-hMSC Microspheres in NOD/SCID Mice Materials and Methods Animal experimentation was conducted with appropriate ethical approval according to institutional regulations. Collagen-hMSC microspheres with 0.5 and 2 mg/ml collagen and 250 cells per microsphere were incubated with 2 μM Calcein AM for 45 minutes for live cell labeling. Twelve NOD/SCID mice (25-30 g) were anaesthetized. An incision was made at the back to create a subcutaneous pocket of approximately 1×1 cm. One thousand collagen-hMSC microspheres were implanted and the incision closed by 5.0 nonabsorbable silk sutures. After 2, 7 and 14 days post-implantation, animals were sacrificed by overdose anesthesia. Skin flaps at the implantation site were harvested and observed under fluorescence microscope to trace for live cells.

Results

The microspheres remained intact and localized at the implantation site while the encapsulated cells were obtained viable in NOD/SCID mice for at least 14 days. Clusters of microspheres encapsulating viable hMSCs, which were stained with vital fluorescent dye, can be identified on day 2, 7 and 14 days post-implantation. Viable hMSCs exhibited their typical elongated morphology. Their human origin was confirmed by the immunopositive staining of human antigen beta2-microglobulin. Immunopositive staining for the human antigen was also found in cells, which are participating in the formation of blood vessels.

Example 10

Extent of Contraction of Fibroblast-Seeded Collagen Gel in the Presence of Glycosaminoglycans (GAGs)

Materials and Methods

Acidic rat-tail collagen solution was neutralized by NaOH and diluted into a final concentration of 0.5 mg/ml. Glycosaminoglycans (Chondroitin-6-sulfate) was added to the gelling mixture at a mass ratio of (1:3, 1:1 and 3:1). All procedures were done in an ice-bath so as to prevent collagen gel information. Human bone marrow derived mesenchymal stem cells (MSCs), and in the presence of full medium, DMEM-LG with 10% FBS and 1% P/S was then suspended thoroughly in the neutralized collagen solution with GAGs as soon as possible to make a final density of 1 or $5 \times 10^5$ cells/ml. The mixture was cast in 4 well culture plate and incubated in a 37° C. incubator for 1 hr to allow for gelation. The gel was detached from the walls of the culture plate using a syringe needle and supplemented with sufficient medium. The size of the gel was measured under a dissection microscope at different time points to record the extent of contraction.

Results

Figure 8A:
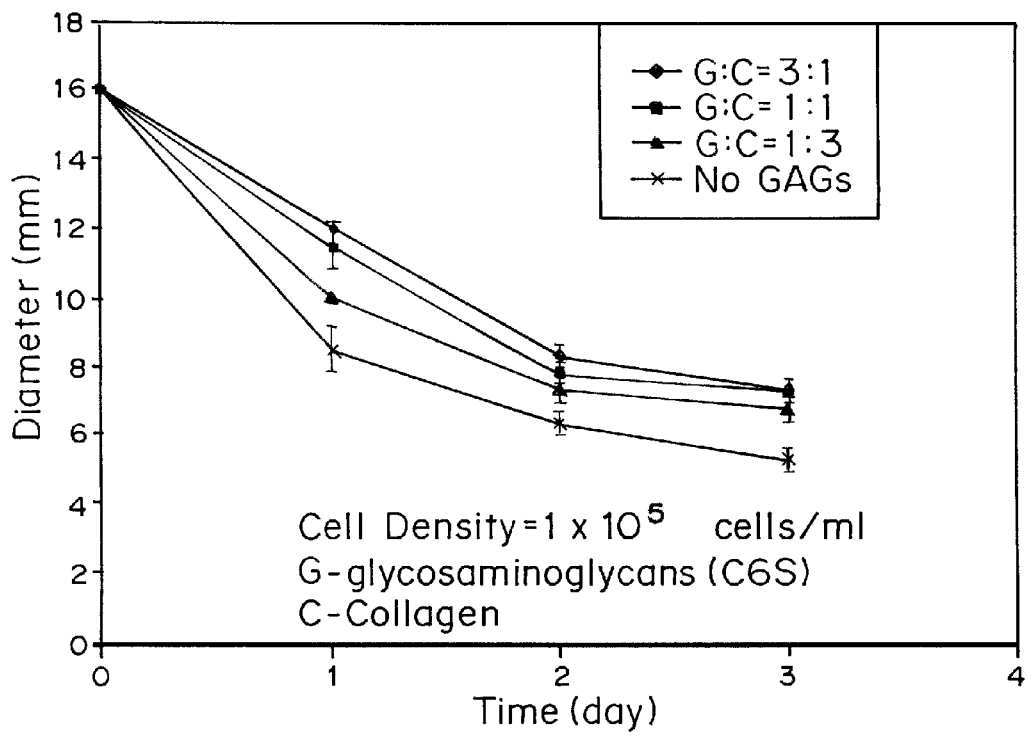
FIGS. 8A and 8B are graphs showing the extent of fibroblast-induced contraction of collagen gel (mm) in the presence of glycosaminoglycans at different cell densities (G:C, 3:1, 1:1, 1:3, no GAG) over time (days).
Figure 8B:
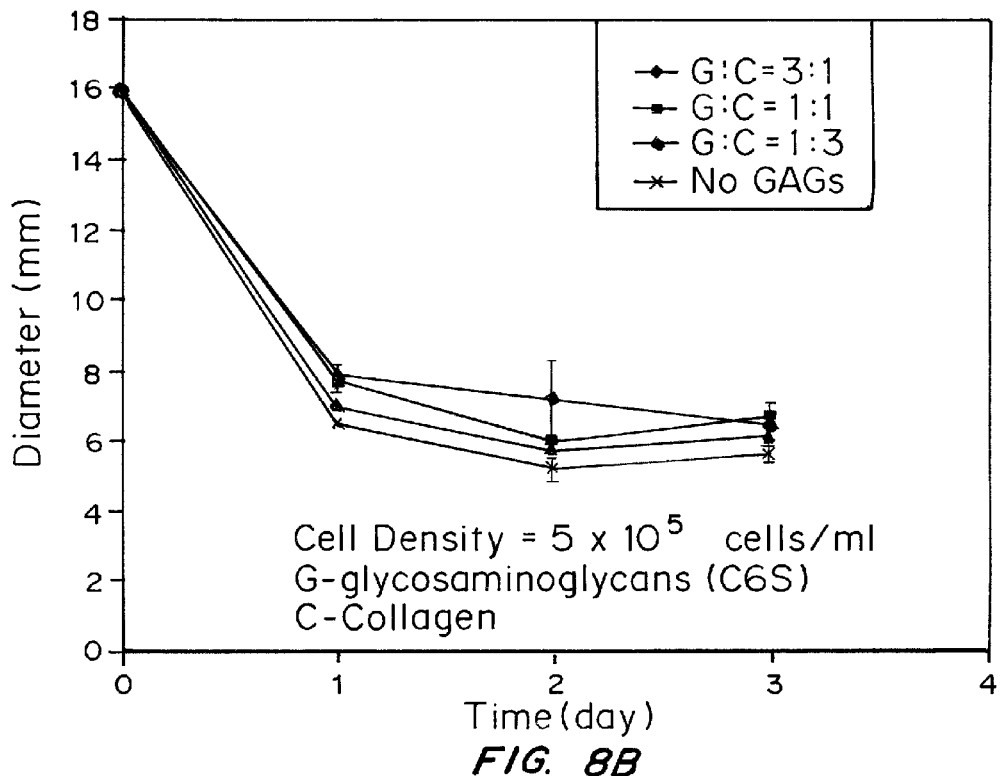

At all cell densities, fibroblasts-seeded gels contracted significantly over time due to the migration and proliferation of cells, as shown by FIGS. 8A and 8B. The presence of a second matrix such as GAGs did affect the cellular responses in collagen gel. In particular, presence of GAGs reduced the extent of fibroblasts-induced gel contraction and was in a dose-dependent manner that a higher mass ratio of GAGs:Collagen resulted in a less extent of contraction, as demonstrated by comparing the results for $1 \times 10^5$ cells/ml in FIG. 8A with the results for $5 \times 10^5$ cells/ml in FIB. 8B.

Example 11

HEK293 Cell Culture and Encapsulation

Materials and Methods

HEK293 cells (Passage 4) were transfected to over-express GDNF. Cells were cultured at 37° C. with 5% $CO_2$ using T75 flask with 10 ml complete Dulbecoo's Modified Eagle Medium—High Glucose (DMEM-HG, 2%, 5% or 10% FBS, 1% PS) and 500 μg/ml G418 Sulfate. Fresh medium and G418 sulfate were replaced every 2 days. These cells were used for the subsequent encapsulation.

The HEK293 cells were trypsinized using 0.25% Trypsin-EDTA. Rat-tail collagen solution type I was neutralized by NaOH and diluted into a final concentration of 4 mg/ml, in the presence of HEK293 cells in DMEM. The cell mixture was kept at 4° C. in an ice bath before use. The dispenser was loaded with the cell mixture and dispensed a small volume of 5 μl at a time onto a collection platform or a bacterial culture dish covered with UV-irradiated parafilm. The microdroplets were allowed to reconstitute into solid microspheres by incubating in a 37° C. incubator with 5% $CO_2$ for 1 hr. The cell-matrix microspheres formed were collected into a DMEM medium containing bath with non-adherent substratum by gently flushing the parafilm with medium. Complete medium was used to suspend the cell-encapsulated capsules in 35 mm petri dish. Cell proliferation, cell viability, GDNF productivity of HEK293 cells in 3D microspheres were compared with that cultured in traditional monolayer cultures.

Results

Morphological Analysis of the Microspheres

Figure 9:
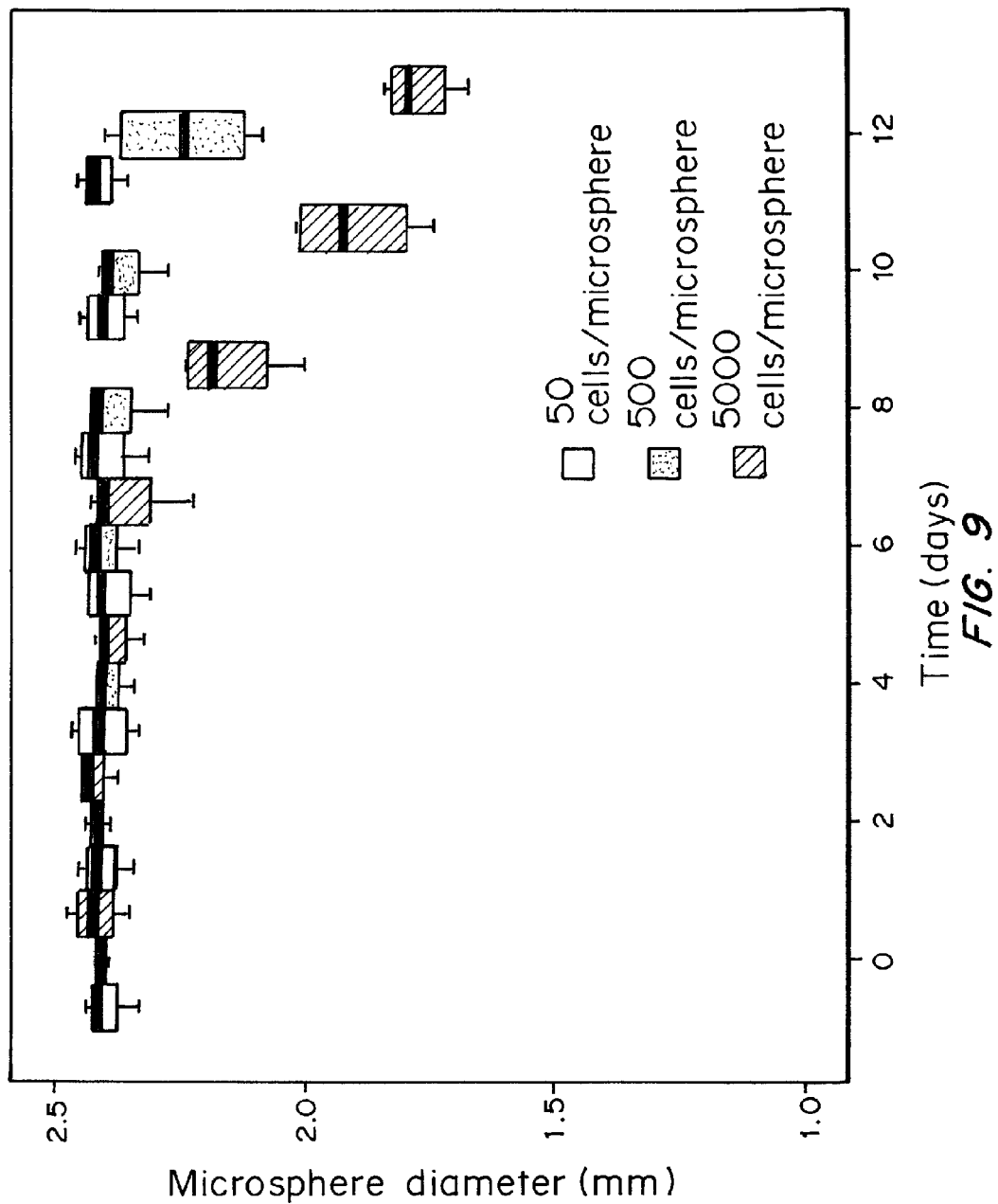
FIG. 9 is a graph showing the temporal change in diameter (mm) of the cell-matrix microspheres encapsulating cells at different densities: 50, 500 and 5000 cells/microsphere over time (days).

The cell-encapsulated capsules were viewed under an inverted microscope. Diameter of the capsules was measured at 40× magnification. The diameters of 5 out of 50 cell-encapsulated capsules in each set up were measured and the average value determined. The rate of contraction of the cell-encapsulated capsules depended on the cell-seeding density, as shown by FIG. 9. With a higher cell-seeding density, the cell-encapsulated capsules contracted at an earlier time point and at a higher rate. Using the high cell-seeding density of 5000 cell/capsule, contraction began at day 4. The mean diameters were 2.42 mm±0.05 and 1.77 mm±0.07 on day 0 and day 12 respectively. For cell-seeding density of 500 cells/microsphere, the mean diameter was 2.4 mm±0.01 on day 0. There were no contractions until day 8 and the mean diameter was 2.4 mm±0.15 on day 12. For the low cell-seeding density of 50 cell/microsphere, the mean diameter of capsule was 2.4 mm±0.04 on both day 0 and day 12. This showed that there were no observable contraction of the microspheres. The percentage changes of the mean diameters were (−)26.9%, (−)6.67% and 0% for cell-seeding density of 5000, 500 and 50 cell/microsphere respectively. Colonies or aggregates of cells started to form at day 6 and the size of the aggregates increased throughout day 8 to day 14.

Example 12

Fate of Encapsulated Cells, Viability and Number of Cells

Materials and Methods

For traditional monolayer cultures, the HEK293 cells were trypsinized using 0.25% trypsin-EDTA. The viability tests were done using the trypan blue staining. The numbers of cells were counted using the hemacytometer. For 3D microspheres, collagens (30 unit/ml) was used to digest the cell-encapsulated capsules. Trypsin/EDTA was then added into the colonies suspension and was incubated at 37° C. with 5% $CO_2$ for 3 min to prepare single cell suspension. Viability test using trypan blue and cell counting were conducted.

Results

Figure 10A:
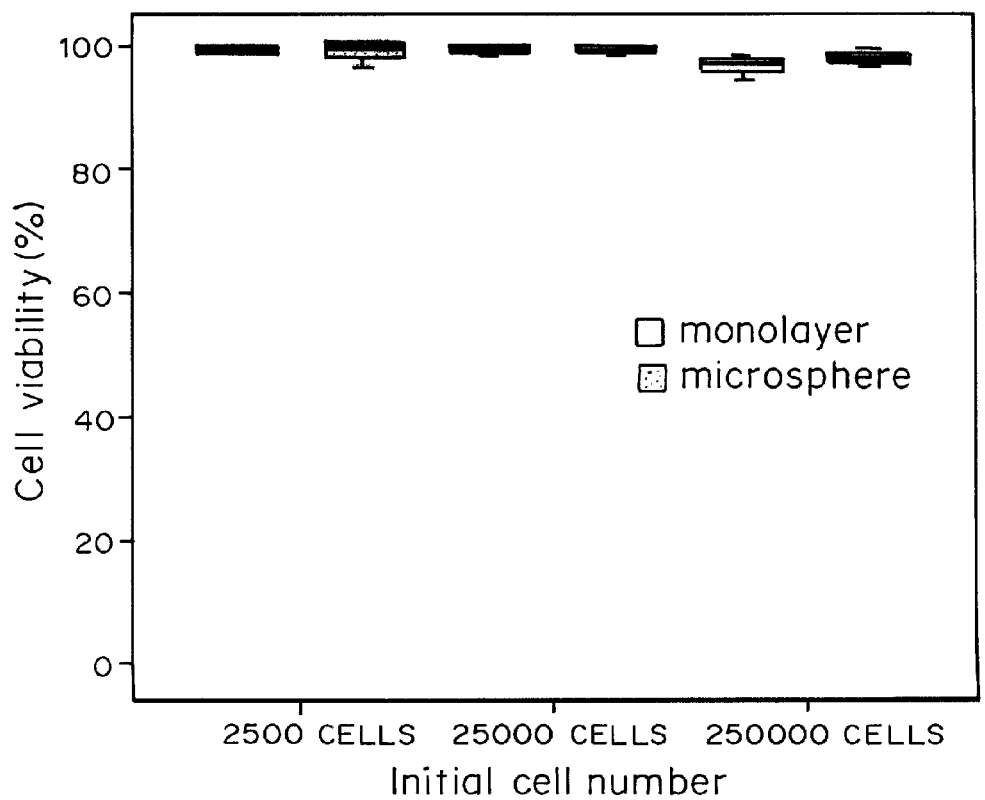
FIGS. 10A and 10B are graphs of the cell viability (10A) and number (10B) of HEK293 cells in 3D microspheres and monolayer cultures with different initial cell numbers: 2500, 25,000, 250,000 cells.
Figure 10B:
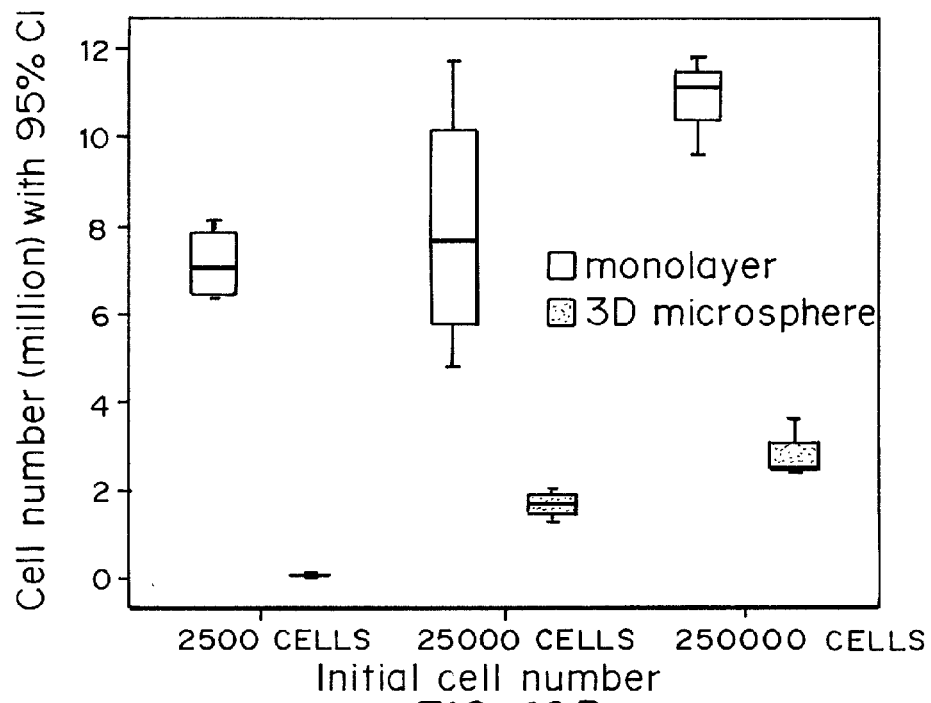

At the early time points, single cells were found inside the capsules. The cell size increased and small aggregates of cells were formed at day 6. Cell aggregation continued to form a network and the morphology of cells resembled those in monolayer culture. The cell viability was shown in FIG. 10A. The viabilities of cells were almost the same at different cell-seeding densities. This showed that cell-seeding density did not affect the cell viability. Moreover, there was no practical difference between the viability of cells in monolayer culture and the viability of the encapsulated cells. The number of cells is shown in FIG. 10B. There was significant difference between the monolayer group and the microsphere group. The proliferation index of the monolayer group was always higher than that of the microsphere group, ranging from 4 to 140 fold. There was also a significant difference between different cell-seeding densities. The interaction between cell density and group was significant as well. The proliferation index of the monolayer group decreased with cell-seeding density but the effect was not obvious in the microsphere group.

Example 13

GDNF Quantification

Materials and Methods

GDNF was measured using the GDNF $E_{max}$® ImmunoAssay System following the instructions provided by the manufacturer (Promega). The 96-well plates were coated with Anti-GDNF Monoclonal Antibody (mAb), which binds soluble GDNF, overnight and at 4° C. without shaking. The captured GDNF is bound by Anti-Human GDNF polyclonal antibody (pAb, 1 μg/ml) and incubated without shaking at 4° C. overnight. After washing, the amount of specifically bound pAb is then detected by incubating with Anti-Chicken IgY, horseradish peroxidase (HRP) conjugate for 2 hr at room temperature with regular agitation. The unbound conjugate is removed by washing, and followed by incubating with the TMB One Solution, a chromogenic substrate, for 15 min at room temperature without shaking. The reaction is stopped by adding 1N HCl. The absorbance at 450 nm was measured using a microplate reader within 30 min after stopping the reaction. The amount of GDNF in the test solutions is proportional to the color generated in the oxidation-reduction reaction. This ELISA system can detect a minimum of 31.2 pg/ml of GDNF and the linear range is from 31 pg/ml to 1000 pg/ml GDNF.

The HEK293 cells were trypsinized using 0.25% Trypsin-EDTA. For monolayer cultures, $2.5\times10^4$ HEK293 cells were seeded onto the 6-well plate with 2 ml complete medium (DMEM, 10% FBS, 1% PS) and 500 μg/ml G418 sulfate. For 3D cultures, microspheres were formed as described above. The cell-seeding density was 500 cells/microsphere and the number of microsphere per 35 mm petri dish was 50. The microspheres were suspended in petri dishes with 2 ml complete medium (DMEM, 10% FBS, 1% PS) and 500 μg/ml G418 sulfate. Different time points included day 2, 4, 8, 10, 14. For both monolayer and microsphere cultures, there were four samples per each time point (n=4). Medium was collected and replaced every 2 days in all set up for GDNF quantification.

The HEK293 cells were trypsinized using 0.25% Trypsin-EDTA. For monolayer cultures, $2.5\times10^3$, $2.5\times10^4$ or $2.5\times10^5$ HEK293 cells were seeded onto the 6-well plate with 2 ml complete medium (DMEM, 10% FBS, 1% PS) and 500 μg/ml G418 sulfate. For 3D cultures, the microspheres were formed as stated in Example 2. The cell-seeding density was 50, 500 or 5000 cells/microsphere. Fifty microspheres were suspended in each 35 mm petri dish with 2 ml complete medium (DMEM, 10% FBS, 1% PS) and 500 μg/ml G418 sulfate. The initial cell number for the 3D cultures is the same as that in monolayer cultures. For both monolayer and 3D cultures, there were four samples per each initial cell number group (n=4). Medium was collected and replaced every 2 days in all groups for GDNF collection and subsequent quantification. Cell viability test and cell counting were conducted on day 12.

The HEK293 cells were trypsinized using 0.25% trypsin-EDTA. For monolayer cultures, $2.5\times10^4$ HEK293 cells were seeded onto the 6-well plate with 2 ml medium having different serum percentage (2%, 5%, 10%) and 500 μg/ml G418 sulfate. For 3D cultures, microspheres were formed as stated in Example 2. The cell-seeding density was 500 cell/microspheres and there were 50 microspheres per 35 mm petri dish equivalent to an initial cell number of $2.5\times10^4$ cells. The microspheres were suspended in 2 ml medium having different serum percentage (2%, 5%, 10%) and 500 μg/ml G418 sulfate. For both monolayer and 3D cultures, there were four samples per each serum percentage (n=4). Medium was collected and replaced every 2 days in all set up for GDNF quantification. Cell viability test and cell counting were conducted on day 12.

Results

Figure 11A:
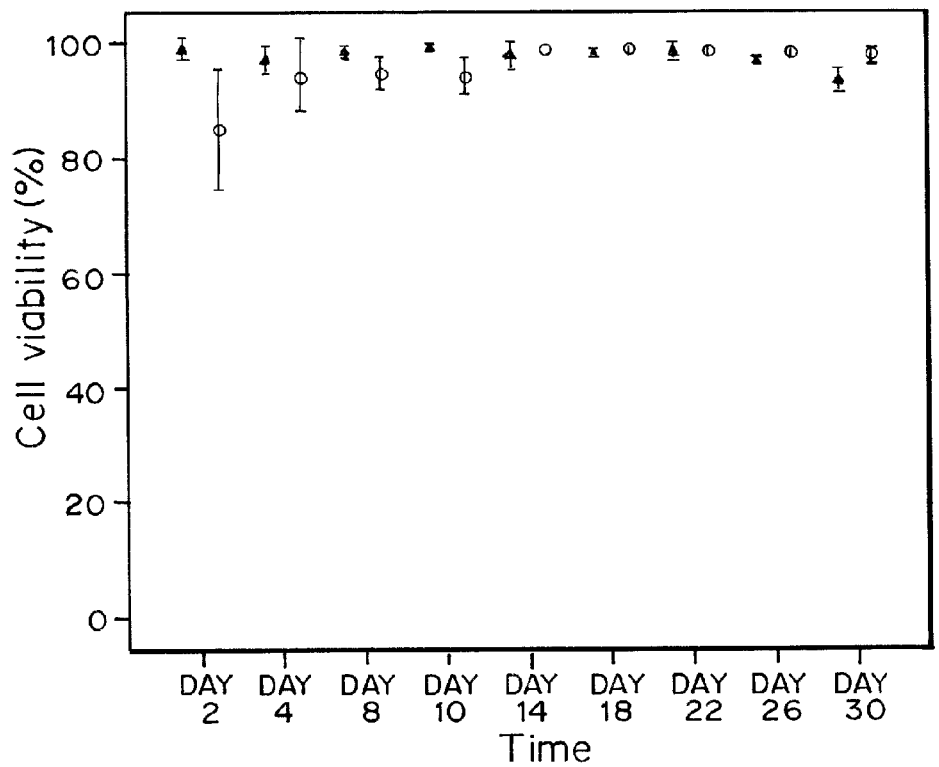
FIGS. 11A and 11B are graphs showing the temporal change in cell viability, percent (3A) and cell number (3B) of HEK293 cells in 3D microsphere and monolayer cultures over time in days.
Figure 11B:
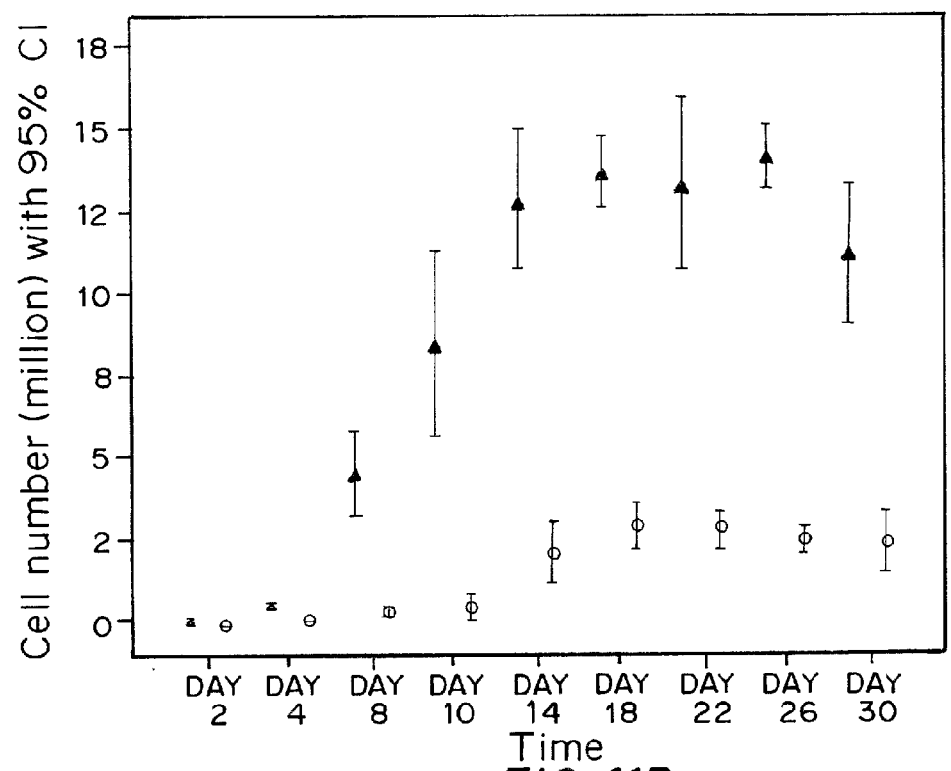

The cell viability and number of HEK293 cells in both monolayer and 3D microspheres at each time point (Day 2, 4, 8, 10, 14, 18, 22, 26 and 30) are shown in FIGS. 11A and 11B, respectively. The cell number of the monolayer group was always higher than that of the microsphere group and there was a significant difference between them. Apart from an initial lower cell viability of around 80% in 3D microspheres, the cell viability of all groups in all subsequent time points was close to 100%. The accumulative secretion of GDNF was linearly proportional to time in both the monolayer group and the microsphere group (FIG. 12). There was a significant difference in accumulative secretion of GDNF between monolayer group and microsphere group. Post hoc testing showed a significant difference between day 2 and day 4 with all other time points. The secretion rates of GDNF in different groups over different time points were shown in FIG. 12B. For both monolayer and microsphere groups, the secretion rate of GDNF continued to increase until day 8. There was a significant difference between the secretion rate of monolayer group and that of the microsphere group. The secretion rates of GDNF from HEK293 cells in the 3D microspheres were 67, 12, 10, 10 and 3.5 times that from monolayer cultures for day 2, 4, 8, 10 and 14, respectively. This demonstrates significantly higher productivity in 3D microspheres.

Figure 12A:
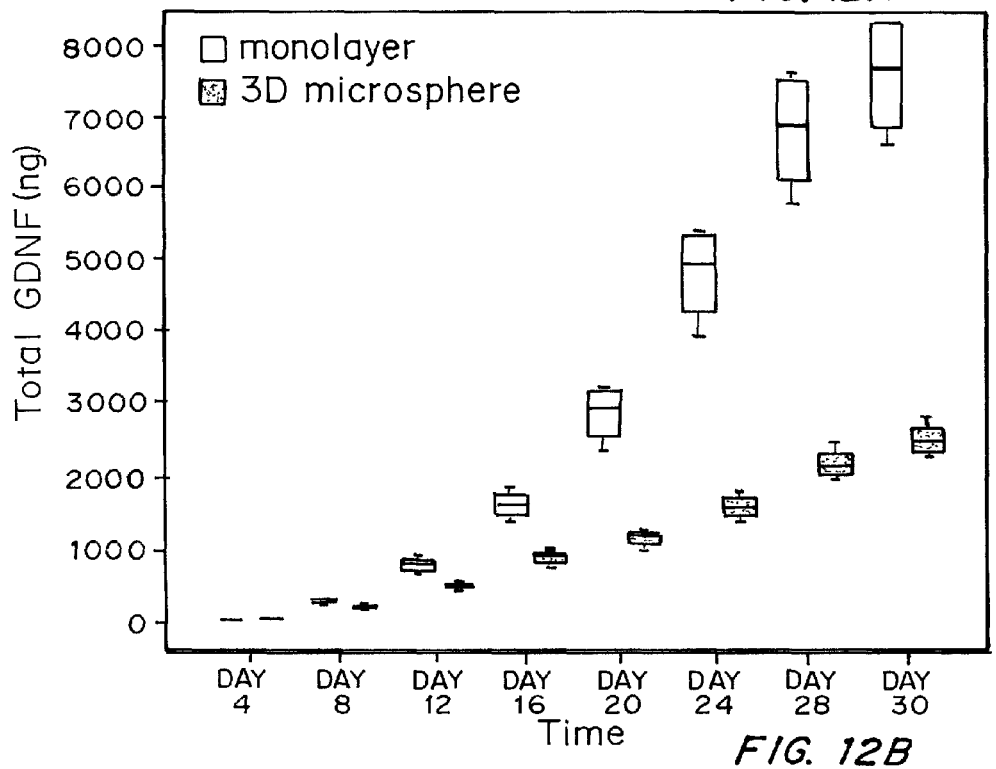
FIGS. 12A-F are graphs showing GDNF productivity in HEK293 cells. Accumulative secretion (ng GDNF) (FIG. 12A) and rate of secretion (ng GDNF/million cells/day) (FIG. 12B) of GDNF from HEK293 cells in 3D microspheres and monolayer cultures over time in days. Total GDNF (ng) secreted from (FIG. 12C) and secretion rate (ng GDNF/million cells/day) of HEK293 cells in 3D microspheres and monolayer cultures with different initial cell numbers (FIG. 12F). Total GDNF (ng) secreted from (FIG. 12E) and secretion rate (ng GDNF/million cells/day) of HEK293 cells in 3D microspheres and monolayer cultures (ng GDNF/million cells/day) with different serum concentrations: 2, 5, and 10%.
Figure 12B:
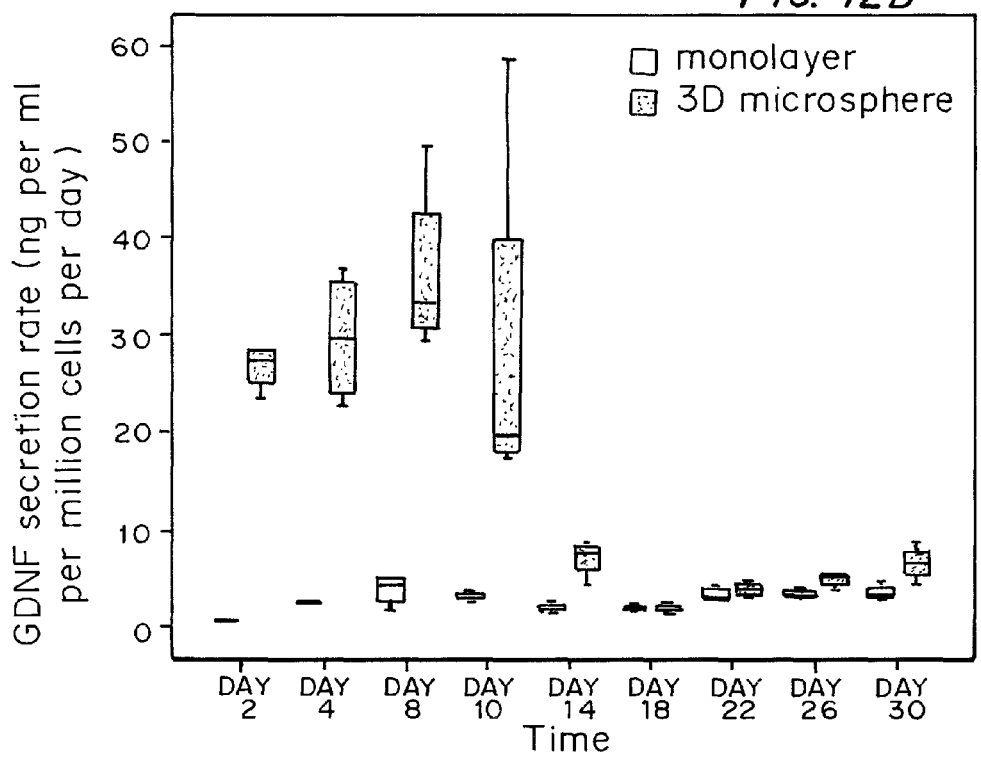
Figure 12C:
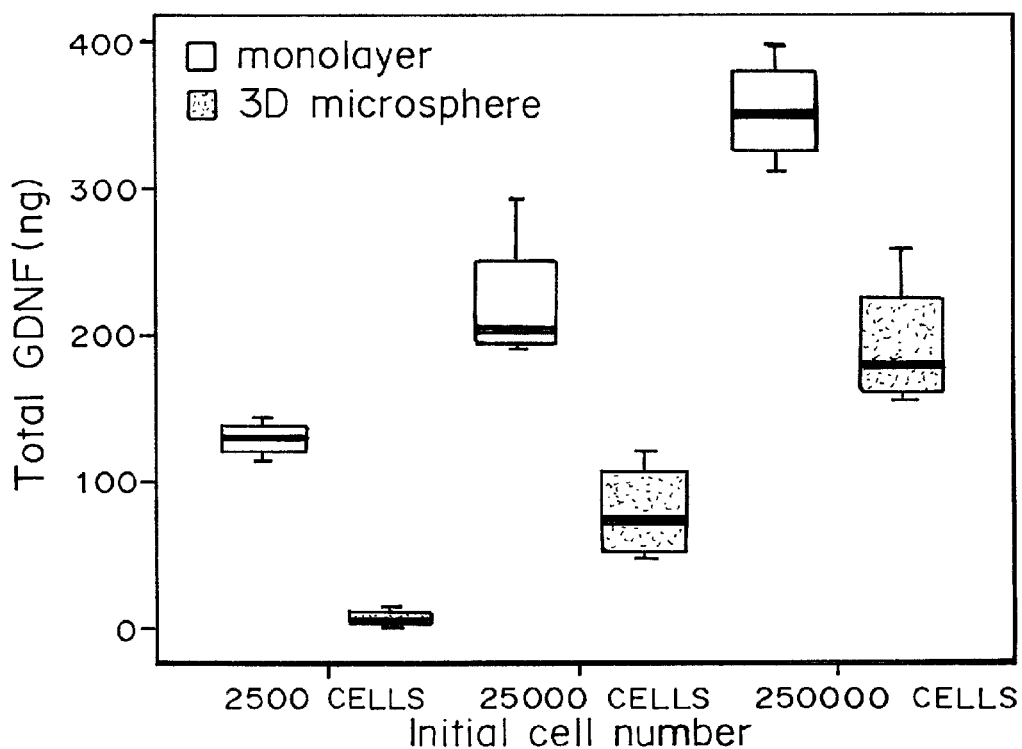
Figure 12D:
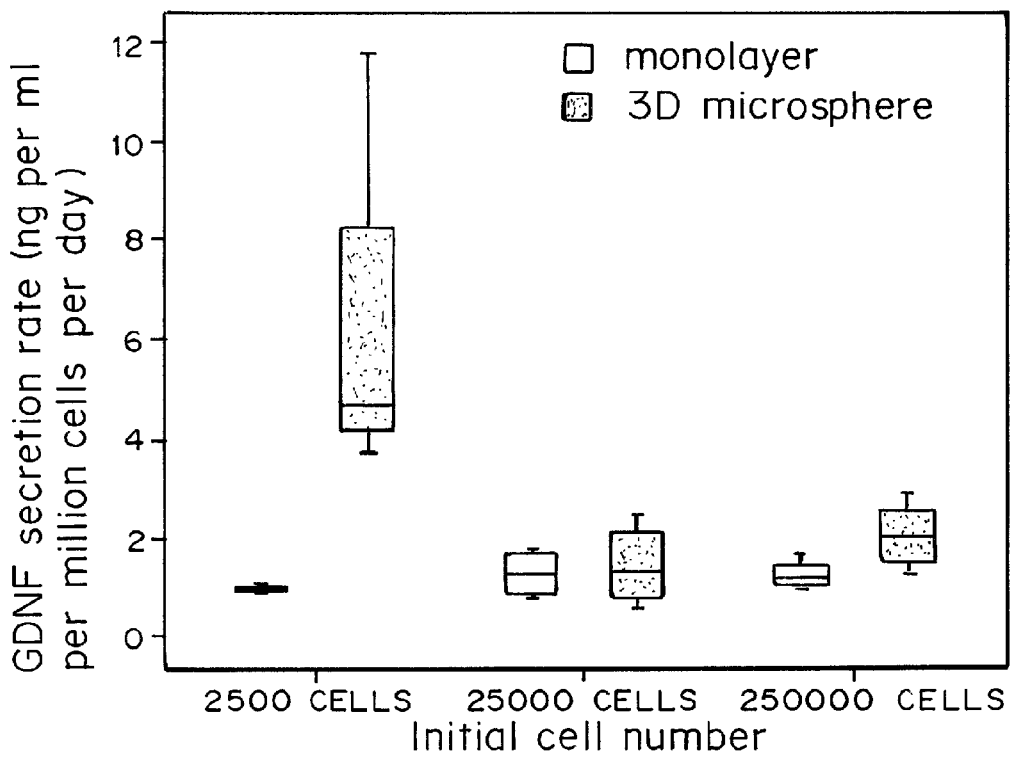

The total GDNF secretion of both monolayer and microsphere groups were linearly proportional to the cell-seeding density (FIG. 12C). There was a significant difference in total GDNF secretion between the monolayer and microsphere groups, and among different cell densities. The total GDNF secretion of the monolayer group is higher than that of the microsphere group, due to the large difference in cell number. At each cell-seeding density, the number of cell in monolayer group is about 7-20 times higher than the number of cell in microsphere group at day 12. However, the secretion rate of GDNF from HEK293 cells was found to be higher than that from monolayer cultures in all groups (FIG. 12D) and the difference was statistically significant between monolayers and microsphere cultures and among groups with different initial cell numbers.

Figure 12E:
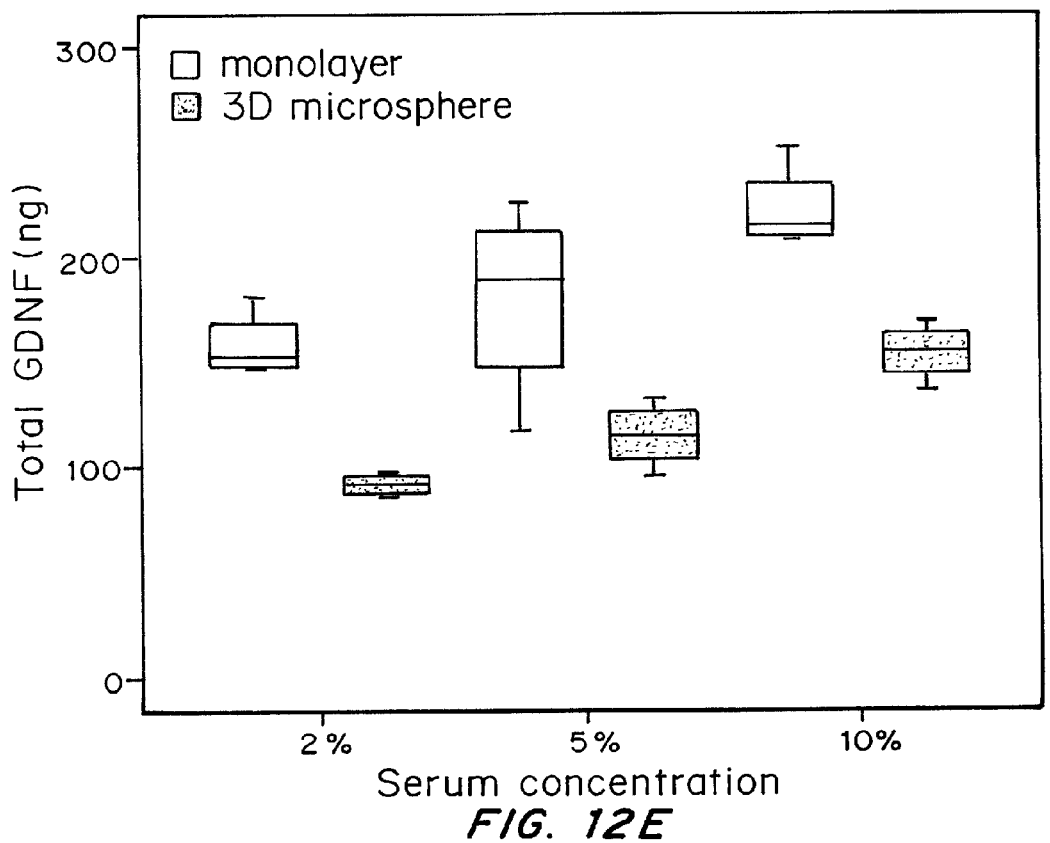
Figure 12F:
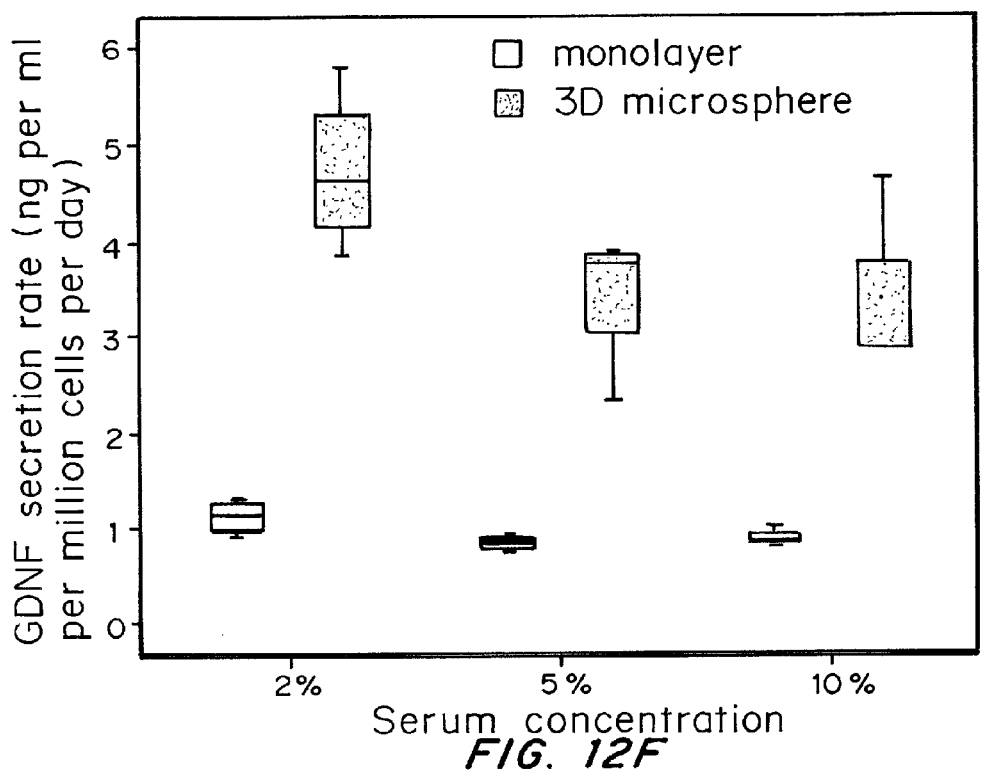
Figure 13A:
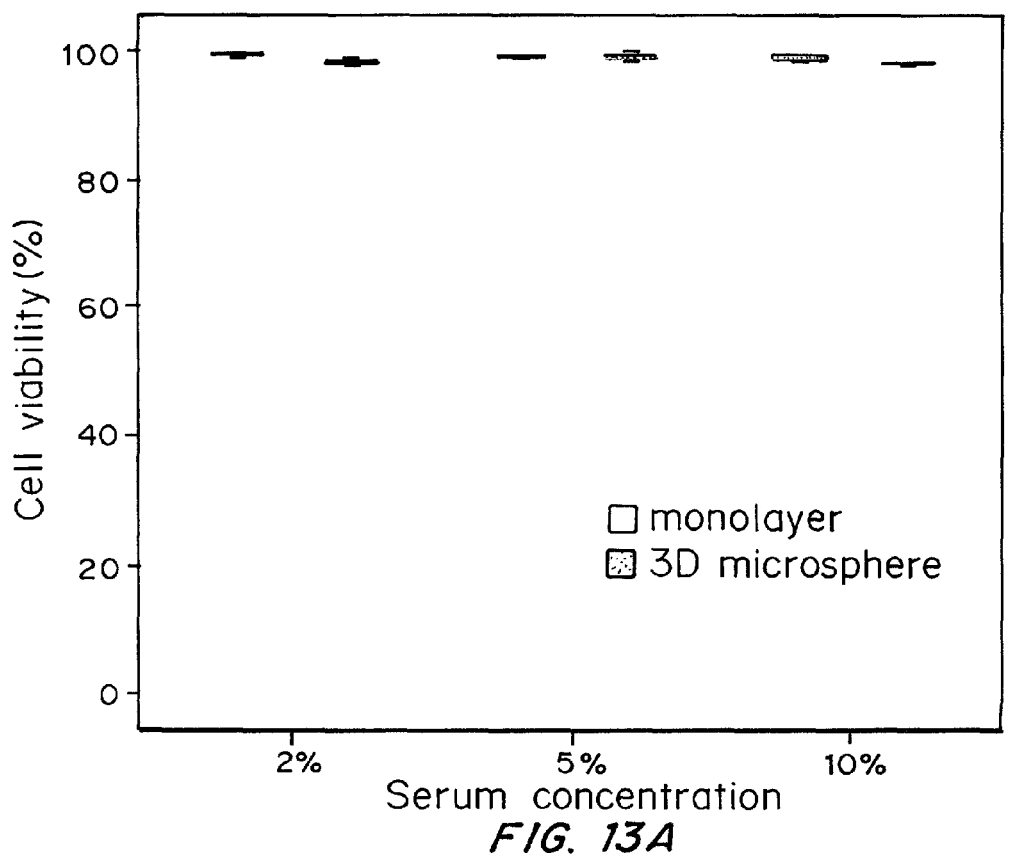
FIGS. 13A and 13B are graphs of the cell viability, percent (13A) and number (13B) of HEK293 cells in 3D microspheres and monolayer cultures with different serum concentrations: 2, 5, and 10%.
Figure 13B:
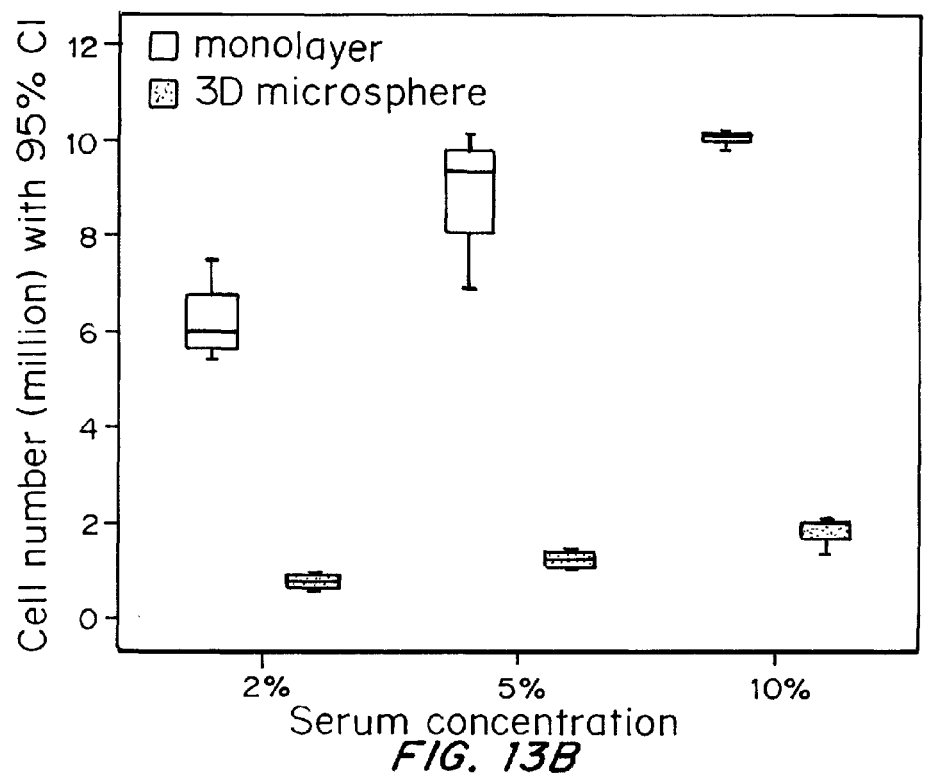

The total GDNF secreted from day 0 to day 12 was linearly proportional to the serum percentage in medium in both monolayer and microsphere groups (FIG. 12E). There were significant differences in total GDNF secretion between the monolayer and microsphere groups and among different serum percentages in medium. The total GDNF secretion in monolayer group was always higher than that in microsphere group and the differences were less than 2 folds at all serum percentages. There was no interaction between group and serum percentage in medium. However, the secretion rate of GDNF from HEK293 cells per million cells per day (FIG. 12F) was significantly higher than that from monolayer cultures at all serum percentages. The difference in GDNF secretion rate in 3D microspheres was more than 4 folds in all serum concentrations indicating that the enhanced productivity of HEK293 cells in 3D microspheres was independent of the serum percentage. It also demonstrated that the encapsulated cells secreted the highest rate of GDNF when they were sustained with medium with 2% serum. The cell viability and number of HEK293 cells in microspheres cultured with different serum concentration are shown in FIGS. 13A and 13B, respectively and the viability in all serum concentrations showed almost 100% (FIG. 13A) indicating that the cell viability was not significantly affected by reducing the serum concentration, as a result, reducing serum concentration can be used to ease the downstream purification steps of the secreted proteins.

Example 14

Bioactivity Assay of GDNF in Conditioned Medium of HEK293 Cells

Materials and Methods

PC 12 cells were grown on 24-well plates in 81.5% F12K medium, supplemented with 15% House serum, 2.5% Fetal bovine serum and 1% PS. Conditioned medium containing the secreted GDNF was mixed with the full medium for PC12 culture at 1:1 volume ratio and used to culture the PC12 cells. The cells were plated at a density of approximately 3000 cells (in 800 ul) per well. After 2 days, the cells were fixed for visualization under the phase microscope. Cells with neurite outgrowth longer than one body length of the cell were regarded as positive results. Standard GDNF with known concentrations were also used as positive controls. Full medium without conditioned medium was used as negative control.

Results

Both GDNF standards (10 and 50 ng/ml) and all conditioned medium samples showed neurite growth in PC12 cells while the negative controls showed no neurite outgrowth. This demonstrated that GDNF released by the HEK293 cells into the conditioned medium does retain their bioactivity.

Example 15

Bioactivity Assay of GDNF in Conditioned Medium of HEK293 Cells

GDNF-secreting HEK293 cells were encapsulated in 3D collagen microspheres and cultured for 14 days. The microspheres were fixed in 4% paraformaldehyde for 3 hours followed by 30% sucrose solution for overnight before cryosections of 10 m thick were prepared. Immunohistochemistry of GDNF was conducted to confirm its secretion using a primary antibody, chicken anti-human GDNF polyclonal antibody (Promega) at 1:100-1:50 dilution and a secondary antibody, rabbit anti-chicken IgY (Promega) at 1:100-1:50 dilution. HRP-DAB substrate system was used to visualize the immuno-positively stained GDNF inside the microspheres. The synthesis of GDNF was confirmed by immunohistochemistry. Immunopositive staining of GDNF was localized at the cell colonies inside the 3D microspheres.

Example 16

Optimization of Formulation Parameters of Cell-Matrix Microspheres

Materials and Methods

Culture medium, NaOH, collagen solution, chondroitin sulfate solution and cell suspension were added and mixed in order, and microspheres of 100 ul of the mixture were prepared as described in Example 1. The microspheres were cultured in normal medium for 1 day and then changed to chondrogenic differentiation medium (DMEM high glucose, 10 ng/ml recombinant human transforming growth factor beta 3 (Merck), 100 nM dexamethasone (Sigma), 6 µg/ml insulin (Merck), 100 mM 2-phospho-L-ascorbate (Fluka), 1 mM sodium pyruvate (Gibco), 6 µg/ml transferrin (Sigma), 0.35 mM L-proline (Merck) and 1.25 mg/ml bovine serum albumin (Sigma)).

The microspheres were cultured for 21 days, with medium changed every two days. After 21 days of culture, the samples were either processed for immunohistochemistry and histology for qualitative analysis or digested in papain solution (300 µg/ml papain in 50 mM PB, containing 5 mM L-cysteine and 5 mM EDTA) at 60° C. overnight for quantitative analysis of chondrogenesis. 1,9-Dimethylmethylene blue (DMMB) assay was used for GAG quantification. In brief, 1 ml of DMMB dye solution was added to the sample digest in a tube and the content was mixed on a shaker for 30 minutes. The tube was centrifuged at 13.2 k rpm for 10 minutes to form the GAG-dye complex precipitate. The precipitate was resuspended in 200 µl of dissociation reagent and mixed by vortex and the absorbance at 656 nm was measured. From the digestion mixture, DNA content was also quantified by a fluorometric assay. In brief, 100 µl of Hoechst 33258 dye solution was added to the sample digest and fluorescence measurement was made with excitation and emission at 365 nm and 458 nm respectively. The GAGs content was then normalized by DNA content.

Results

Figure 14A:
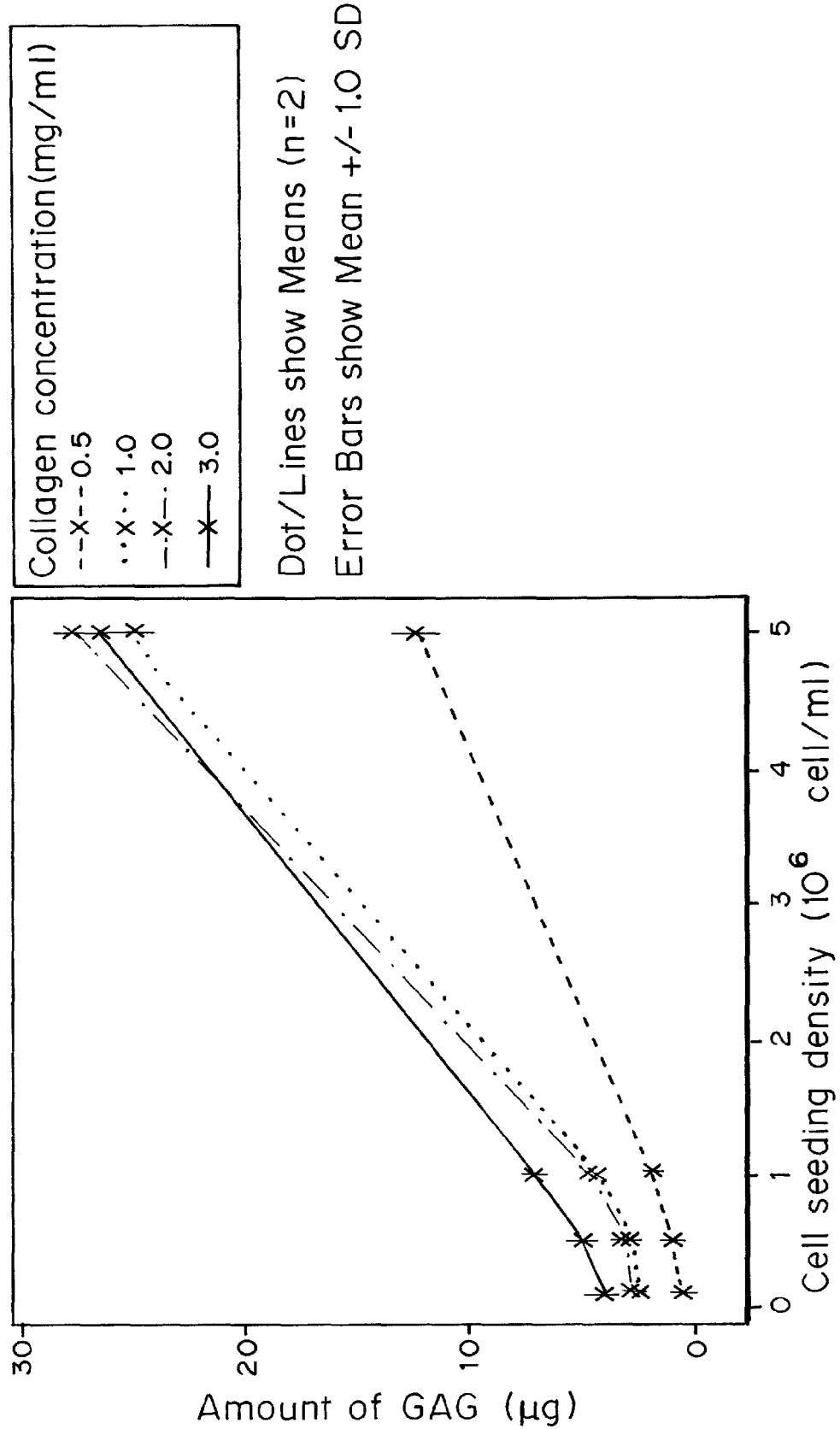
FIGS. 14A and 14B are graphs of the amount (micrograms) GAG (FIG. 14A) and GA/DNA (FIG. 14B) in samples with different cell seeding densities, 0, 0.5, 1, and $5\times10^6$/ml, for different collagen concentrations: 0.5, 1.0, 2.0 and 3.0 mg/ml.
Figure 14B:
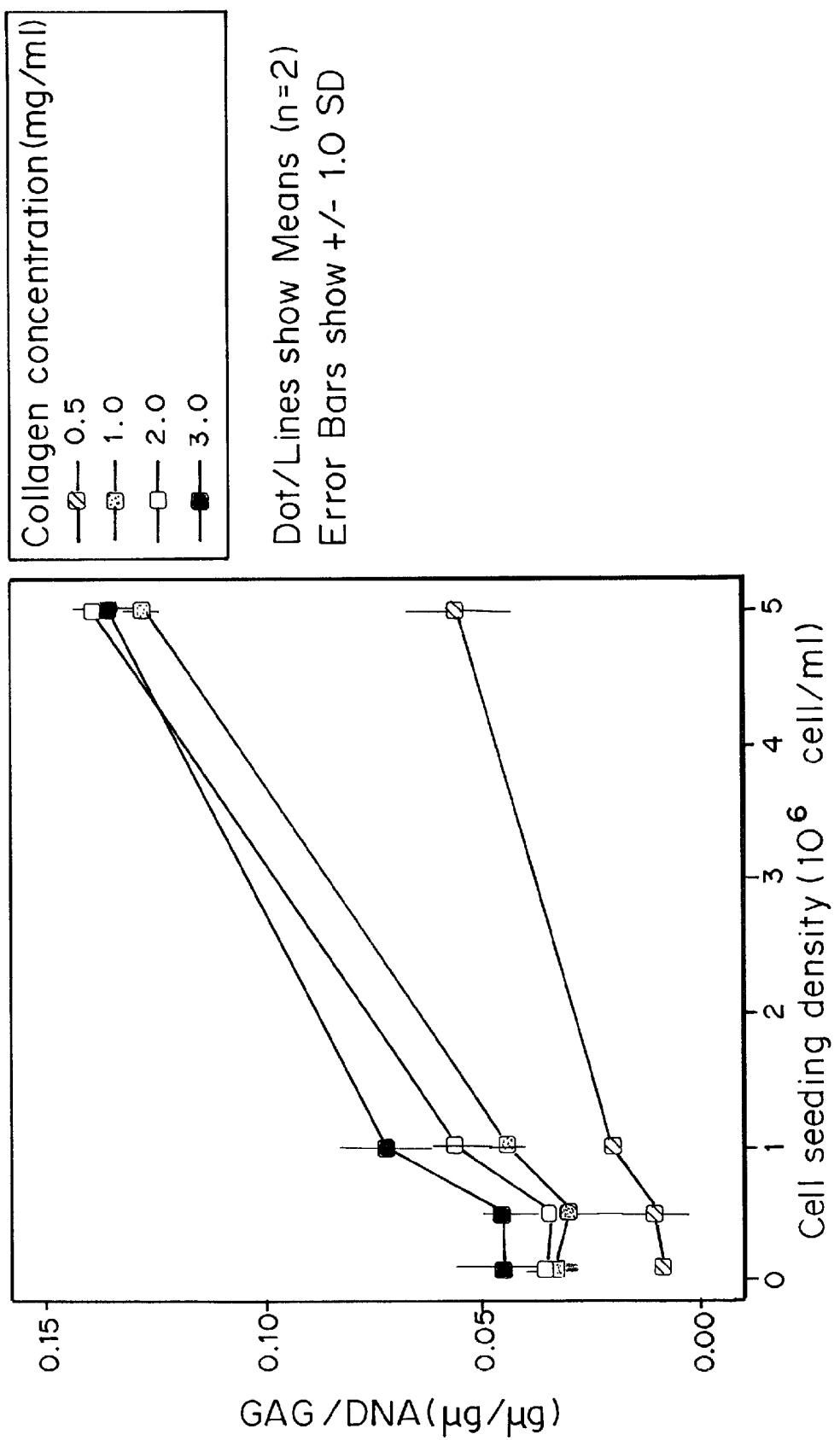

The amount of GAGs deposited into the collagen microspheres increased with increasing cell seeding density and collagen concentration, as shown in FIG. 14A. Statistical analysis shows that the difference among the four cell seeding density groups and among collagen density groups are all significant ($p<0.05$). When normalized by DNA content, the amount of GAG/DNA also increased with increasing cell seeding density and collagen concentration, as demonstrated by FIG. 14B. Statistical analysis also shows significant difference among various groups ($p<0.05$).

We claim:

1. Cell-matrix microspheres consisting of cells and an extracellular matrix material (ECM), wherein the ECM forms a nanofibrous matrix in which the cells are embedded as a result of a phase change of the ECM after mixing of the ECM with the cells and formation of droplets of the ECM-cell mixture.

2. The microspheres of claim 1, wherein the ECM provides support to the cells, interacts with the cells to allow cell growth without introducing toxicity and permits cell migration from the microspheres for growth.

3. The microspheres of claim 1, wherein the ECM is collagen.

4. The microspheres of claim 1, wherein the ECM can be induced to reconstitute into solid form under specific conditions that are mild enough to support cellular survival and growth.

5. The microspheres of claim 1, wherein the ECM comprises a first ECM and a second ECM selected from the group consisting of proteoglycans and glycosaminoglycans (GAGs).

6. The microspheres of claim 5, wherein the second ECM comprises materials selected from the group of materials consisting of cartilage, fibrin, elastin and hyaluronic acid.

7. The microspheres of claim 5, wherein the first ECM can interact with living cells or with the second ECM in such a way that the interaction leads to change in volume or dimension, ECM density, cell density, mechanical property or stability of the microspheres.

8. The microspheres of claim 1, wherein the cells comprise mature cells, mesenchymal cells or stem cells isolated from bone marrow, skin, GI tract, adipose tissue, placenta, intervertebral discs, cartilage, muscles, skin, tendon, ligament, and nerve.

9. The microspheres of claim 1, wherein the cells are bone marrow-derived mesenchymal stem cells (MSCs), either autologous or allogeneic from HLA-matched donors.

10. The microspheres of claim 1, wherein the cells are genetically engineered or selected for production of biomolecules.

11. The microspheres of claim 1, further comprising a growth-stimulating factor present in a material selected from the group consisting of human serum, platelet rich plasma and other blood products.

12. The microspheres of claim 1, further comprising a differentiation factor.

13. The microspheres of claim 1 further comprising a therapeutic, prophylactic or diagnostic agent.

14. A method for manipulating cell migration from microspheres formed of ECM encapsulated cells as defined by claim 1, comprising the following steps:
providing the microspheres of claim 1;
providing a mechanical support for the microspheres;
plating the microspheres on the support, thereby forming a culture system, wherein each microsphere is kept at a distance from each other;

adding a culture medium into the culture system for holding the microspheres;

allowing cell migration from the microspheres; and releasing the microspheres from the medium after an extended period of time.

15. The method of claim 14, further comprising cryopreserving or re-encapsulating the cells which migrate out from the microspheres.

16. A method for injecting or implanting cell-matrix microspheres as defined by claim 1 into tissues of animals or humans comprising:

providing the cell-matrix microspheres of claim 1 in a pharmaceutically acceptable medium; and injecting or implanting the cell-matrix microspheres and pharmaceutically acceptable medium in tissue.

17. The method of claim 16 wherein the cells are mesenchymal stem cells.

18. The method of claim 17 further comprising inducing the cells to differentiate prior to injection or implantation.

19. A method for production of a biomolecule comprising:

culturing cells as part of the cell-matrix microspheres of claim 1, wherein the cells are capable of producing a biomolecule.

* * * * *